US011439575B2

(12) United States Patent
Gregolin et al.

(10) Patent No.: US 11,439,575 B2
(45) Date of Patent: Sep. 13, 2022

(54) HAIR COSMETIC COMPOSITIONS CONTAINING THIOL-BASED COMPOUNDS AND METHODS FOR CLEANSING AND TREATING HAIR

(71) Applicant: L'OREAL, Paris (FR)

(72) Inventors: Marina Tavares Gregolin, Rio de Janeiro (BR); Ana Paula Leme De Magalhaes, Rio de Janeiro (BR); Bruno Maiko Sato, Rio de Janeiro (BR); Erika Alegrio Jarque Petali, Rio de Janeiro (BR); Sintia Aguiar Martins, Rio de Janeiro (BR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/338,073

(22) PCT Filed: Sep. 30, 2016

(86) PCT No.: PCT/BR2016/050247
§ 371 (c)(1),
(2) Date: Mar. 29, 2019

(87) PCT Pub. No.: WO2018/058208
PCT Pub. Date: Apr. 5, 2018

(65) Prior Publication Data
US 2019/0231665 A1  Aug. 1, 2019

(51) Int. Cl.
A61K 8/44 (2006.01)
A61K 8/42 (2006.01)
(Continued)

(52) U.S. Cl.
CPC ............ A61K 8/442 (2013.01); A61K 8/42 (2013.01); A61K 8/46 (2013.01); A61K 8/463 (2013.01);
(Continued)

(58) Field of Classification Search
CPC .......... A61K 8/46; A61K 8/463; A61K 8/737; A61K 8/442; A61K 8/42; A61K 2800/48;
(Continued)

(56) References Cited

U.S. PATENT DOCUMENTS 9,018,150 B1 * 4/2015 Rizk ..................... A61K 8/416
510/119
2003/0104020 A1 * 6/2003 Davison ................. A61Q 19/00
424/401
(Continued)

FOREIGN PATENT DOCUMENTS

DE 102010055766 A1 6/2012
DE 102010055767 A1 6/2012
(Continued)

OTHER PUBLICATIONS

DE 102010055767 A1, 2012, Provided by applicant on 1449.*
(Continued)

Primary Examiner — Blessing M Fubara
(74) Attorney, Agent, or Firm — Polsinelli PC

(57) ABSTRACT

The present invention relates to a hair cosmetic composition for cleansing and conditioning hair fibers, in particular human hair fibers, the hair cosmetic composition comprising anionic surfactants, amphoteric surfactants, thiol-based compounds selected from thiolactic acid, thiolactic acid derivatives, their salts, and mixtures thereof, thickening agents; nonionic surfactants; and water; wherein the pH of the composition ranges from about 2 to less than 7. The invention also concerns a method for imparting hair care benefits to hair fibers such as straightening effects, volume reduction, frizz control, manageability, cosmeticity, and smooth feel, in addition to cleansing and conditioning benefits and a use for hair care employing the cosmetic compositions of the present invention.

19 Claims, 3 Drawing Sheets

(51) Int. Cl.
    *A61Q 5/02*     (2006.01)
    *A61K 8/73*     (2006.01)
    *A61K 8/46*     (2006.01)

(52) U.S. Cl.
    CPC ............... *A61K 8/737* (2013.01); *A61Q 5/02* (2013.01); *A61K 2800/48* (2013.01); *A61K 2800/596* (2013.01); *A61K 2800/5922* (2013.01)

(58) Field of Classification Search
    CPC ...... A61K 2800/596; A61K 2800/5922; A61Q 5/02
    See application file for complete search history.

(56) References Cited

U.S. PATENT DOCUMENTS

2005/0238595 A1* 10/2005 Stella ...................... A61K 8/35
                                                                                       424/59
2011/0223125 A1* 9/2011 Hough ...................... A61K 8/86
                                                                                       424/70.12
2014/0318566 A1* 10/2014 Mignon ................. A45D 19/02
                                                                                       132/221
2016/0287502 A1* 10/2016 Goutsis .................. A61Q 5/065

FOREIGN PATENT DOCUMENTS

WO           03086335 A1    10/2003
WO      WO-03086335 A1 * 10/2003   ............... A61Q 5/02

OTHER PUBLICATIONS

International Search Report and Written Opinion dated Dec. 8, 2016 for corresponding PCT Application No. PCT/BR2016/050247.
International Preliminary Report on Patentability dated Apr. 2, 2019 for corresponding PCT Application No. PCT/BR2016/050247.

* cited by examiner

HAIR COSMETIC COMPOSITIONS CONTAINING THIOL-BASED COMPOUNDS AND METHODS FOR CLEANSING AND TREATING HAIR

CROSS-REFERENCE TO RELATED APPLICATIONS

This application is a national stage application (under 35 U.S.C. § 371) of PCT/BR2016/050247, filed Sep. 30, 2016, which is incorporated herein by reference in its entirety.

FIELD OF THE INVENTION

The present application relates to cosmetic compositions for use on keratinous substrates, such as keratin fibers. In particular, it relates to compositions and methods for washing and/or cleansing hair and providing cosmetic and caring benefits to hair.

BACKGROUND OF THE INVENTION

The quality and condition of hair is generally adversely affected by the action of external agents such as sunlight, wind, and humidity, and also by mechanical or chemical treatments, such as brushing, combing, shampooing, dyeing, bleaching, permanent-waving and/or relaxing. Hair is thus damaged by these various factors and may over time become dry, coarse or dull, especially in fragile areas, and more particularly at the ends leading to split ends.

In particular, cleansing compositions typically contain anionic surfactants. Anionic surfactants such as sodium lauryl sulfate have good detergent and foaming properties and are highly effective at removing dirt and oil. However, anionic surfactants raise the cuticle of the hair for deep cleansing, but raised, rough cuticles also lead to frizziness of the hair. In addition, consumers generally find that products containing anionic surfactants can be too drying and damaging on frequent use, and, as a result, choose mild cleansing compositions which have low levels of anionic surfactants. However, such products may not always produce the desired amount of foaming and/or impart a clean feel to the hair. Consumers are therefore still in search of optimized cleansing compositions or cleansing/washing regimens and systems consisting of compositions with good or satisfactory foaming and effective cleansing qualities, and at the same time, provide adequate visual sleekness and smooth and conditioned feel to the hair, and in particular, control, or even eliminate frizziness, and also control or reduce the volume and the apparent mass of the head of hair.

Another area where consumers are always seeking better and unique products is in the area of hair cosmetic products designed to change the appearance, shape or configuration of hair. Examples of such hair cosmetic products are hair relaxers or hair straighteners which can relax or straighten curly or kinky hair, including wavy hair, or reduce/loosen curls while making the hair more manageable, untangled, more easily styled or shaped, and disciplined. Hair relaxers may either be applied in a hair salon by a professional or in the home by the individual consumer.

One type of composition that can be applied onto hair in order to change its shape and make it more manageable is an alkaline composition. Alkaline hair relaxing/straightening involves hydrolyzing the keratin of the hair with various alkaline agents, such as inorganic hydroxides, for instance sodium hydroxide, or organic hydroxides, such as guanidine hydroxide, or organic amines. Hair relaxing/straightening products that employ sodium hydroxide or potassium hydroxide are also called lye-based products and products that use other alkaline agents such as lithium hydroxide, calcium hydroxide, organic hydroxides and other non-hydroxide compounds, for example, organic amines, generally fall under the category of no-lye products. Still, it is desirable to find alternatives to the alkaline lye- and no-lye-based products and process described above which can damage the hair by weakening and/or causing dryness of the hair fibers.

Thus, it is desirable for manufacturers of hair cosmetic products to formulate compositions with ingredients that can effectively cleanse the hair and at the same time, impart good styling/shaping or straightening benefits as well as good hair caring and manageability properties and other cosmetic properties such as conditioning, smooth feel, volume control/reduction, and frizz control/reduction.

However, the discovery of new compositions and processes for treating hair that have enhanced efficacy but impart less or minimal damage to hair, may pose challenges to manufacturers and formulators because the incorporation of new ingredients into the compositions may negatively impacting their performance, cosmetic attributes, texture, and formulation stability. In addition, the acidity/alkalinity and/or pH is an important consideration for these products. New processes for treating and changing the shape of hair may also impact the performance of the compositions, processing times and quality of use. Thus, manufacturers of such products continuously test the use of new raw materials and ingredients or new product forms and seek to re-formulate and create new products with the desired qualities, while still remaining stable and safe to use.

SUMMARY OF THE INVENTION

The present invention is directed to a hair cosmetic composition, the composition comprising:
  a) at least one anionic surfactant
  b) at least one amphoteric surfactant;
  c) at least one thiol-based compound selected from thiolactic acid, thiolactic acid derivatives, their salts, and mixtures thereof;
  d) at least one thickening agent;
  e) at least one nonionic surfactant; and
  f) water;
wherein the pH of the composition ranges from about 2 to less than 7.

The present invention is also directed to processes for treating the hair involving the application of the above-described composition onto hair.

BRIEF DESCRIPTION OF THE DRAWINGS

Implementations of the present technology will now be described, by way of example only, with reference to the attached figures, wherein.

Figure 1:
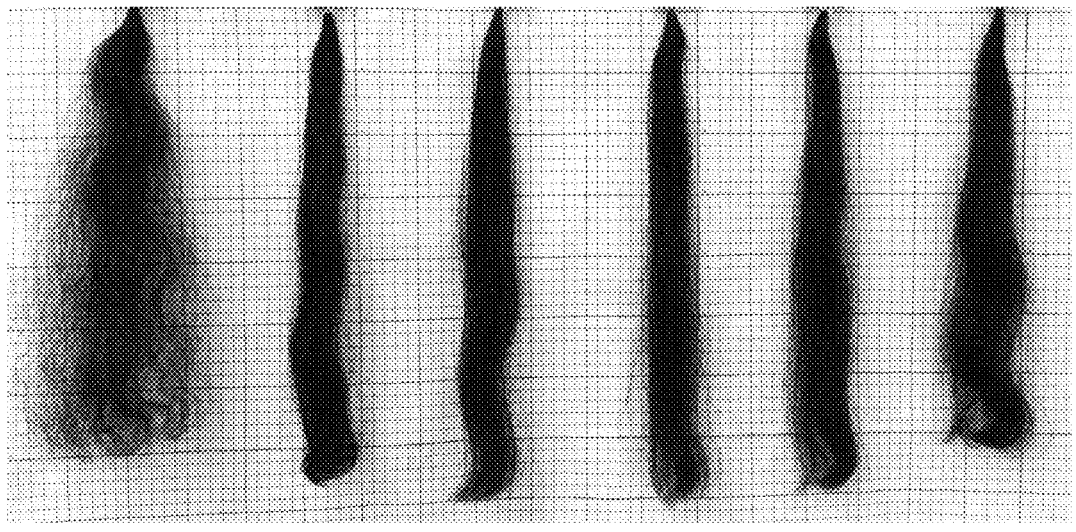
FIG. 1 provides images of hair swatches treated according to one application or treatment cycle including applying inventive or comparative sulfate-based shampoo formulas onto hair and heating the hair at a temperature of equal to or greater than 50° C.

It should be understood that the various aspects are not limited to the arrangements and instrumentality shown in the drawings.

DETAILED DESCRIPTION OF THE INVENTION

The present compositions effectively cleansing the hair and provide manageability properties to hair, including one or more of conditioning; straightening effects; frizz control; volume reduction or volume control; styling or shaping effects; curling effects; texlaxing effects; improvement or retention of curl definition; humidity resistance; cosmeticity to the feel; smooth feel; natural feel; less or reduced rough ends; and/or improvement of the appearance of hair.

"At least one" as used herein means one or more and thus includes individual components as well as mixtures/combinations.

"Keratinous substrates" as used herein, includes, but is not limited to keratin fibers such as hair and/or scalp on the human head.

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term 'treat" (and its grammatical variations) as used herein also refers to contacting keratinous substrates such as hair with the compositions of the present disclosure.

A "rinse-off" product refers to a composition such as a hair care composition that is rinsed and/or washed with water either after or during the application of the composition onto the keratinous substrate, and before drying and/or styling said keratinous substrate. At least a portion of the composition is removed from the keratinous substrate during the rinsing and/or washing.

The term "stable" as used herein means that the composition does not exhibit phase separation and/or crystallization.

"Volatile", as used herein, means having a flash point of less than about 100° C.

"Non-volatile", as used herein, means having a flash point of greater than about 100° C.

"Reducing agent" as used herein, means an agent capable of reducing the disulfide bonds of the hair.

"Active material" as used herein with respect to the percent amount of an ingredient or raw material, refers to 100% activity of the ingredient or raw material.

"Substituted," as used herein, means comprising one or more substituents. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Polymers," as defined herein, include homopolymers and copolymers formed from at least two different types of monomers.

"INCI" is an abbreviation of International Nomenclature of Cosmetic Ingredients, which is a system of names provided by the International Nomenclature Committee of the Personal Care Products Council to describe personal care ingredients.

The compositions and methods of the present invention can comprise, consist of, or consist essentially of the essential elements and limitations of the invention described herein, as well as any additional or optional ingredients, components, or limitations described herein or otherwise useful.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present invention, unless otherwise indicated.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

In an embodiment, the present invention is directed to a hair cosmetic composition, the composition comprising:
 a) at least one anionic surfactant
 b) at least one amphoteric surfactant;
 c) at least one thiol-based compound selected from thiolactic acid, thiolactic acid derivatives, their salts, and mixtures thereof;
 d) at least one thickening agent;
 e) at least one nonionic surfactant; and
 f) water;
 wherein the pH of the composition ranges from about 2 to less than 7.

In one embodiment of the present invention, the at least one anionic surfactant is selected from sulfate surfactants, sulfonate surfactants, carboxylic (carboxylate) surfactants, and mixtures thereof.

In one embodiment of the present invention, the at least one anionic surfactant is selected from sulfate surfactants and preferably selected from sodium laureth sulfate, sodium lauryl sulfate, and mixtures thereof.

In one embodiment of the present invention, the at least one anionic surfactant is selected from sulfonate surfactants, carboxylic (carboxylate) surfactants, and mixtures thereof.

In one embodiment of the present invention, the at least one anionic surfactant is a sulfonate surfactant selected from sodium lauroyl sarcosinate, sodium lauryl sulfoacetate, sodium isethionate, sodium cocoyl isethionate, disodium laureth sulfosuccinate, sodium lauroyl methyl isethionate, and mixtures thereof.

In one embodiment of the present invention, the at least one anionic surfactant is not a sulfate surfactant.

In one embodiment of the present invention, the composition is substantially free of anionic surfactants selected from sulfate surfactants ("sulfate-free").

In one embodiment of the present invention, the at least one amphoteric surfactant is selected from (C8-C20)alkylbetaines, (C8-C20)alkylamido (C1-C6)alkylbetaines, sulfobetaines, (C8-C20)alkylsulfobetaines, (C8-C20)alkylamido (C1-C6)alkylsulfobetaines, (C8-C20)alkylamphoacetate, (C8-C20)alkylamphodiacetate, and their salts, and mixtures thereof.

In one embodiment of the present invention, the at least one amphoteric surfactant is selected from coco-betaine, cocamidopropylbetaine, sodium cocoamphoacetate, disodium cocoamphodiacetate, and mixtures thereof.

In one embodiment of the present invention, the at least one thiol-based compound is selected from thiolactic acid.

In one embodiment of the present invention, the at least one thiol-based compound is present in an amount of from about 0.5% to about 15% by weight, preferably from about 0.6% to about 14% by weight, more preferably from about 0.7% to about 12% by weight, even more preferably from about 0.8% to about 10% by weight or from about 1% to about 8% by weight, based on the total weight of the composition.

In one embodiment of the present invention, the at least one thickening agent is selected from cellulose polymers, gums, modified or unmodified carboxyvinyl polymers, polyacrylamides, copolymers of acrylic acid and of acrylamide, sodium salts of polyhydroxycarboxylic acids, optionally crosslinked and/or neutralized 2-acrylamido-2-methylpropanesulphonic acid polymers and copolymers, polyacrylic acid/alkyl acrylate, glucans, modified or unmodified starches, silicas, and mixtures thereof.

In one embodiment of the present invention, the at least one thickening agent is selected from hydroxyethylcellulose (also known as HEC), hydroxymethylcellulose, methylhydroxyethylcellulose, hydroxypropylcellulose (also known as HPC), hydroxybutylcellulose, hydroxyethylmethylcellulose (also known as methyl hydroxyethylcellulose) and hydroxypropylmethylcellulose (also known as HPMC), cetyl hydroxyethylcellulose, hydroxypropyl guar gums, acrylate/C10 C30 alkyl acrylate copolymers, carbomers, polyacrylates, potato starch modified, and mixtures thereof.

In one embodiment of the present invention, the at least one nonionic surfactant is selected from fatty alcohols, alkoxylated fatty alcohols, alkyl(ether)phosphates, alkylpolyglucosides, fatty acid alkanolamides, and mixtures thereof.

In one embodiment, the compositions of the present invention further comprise at least one cationic conditioning polymer selected from cationic cellulose derivatives, cationic gum derivatives, polymer derivatives of diallyldimethyl ammonium chloride, polymer derivatives of methacrylamidopropyltrimethylammonium chloride, and mixtures thereof, and preferably from polyquaternium-7, polyquaternium-10, guar hydroxypropyltrimonium chloride, and mixtures thereof and present in an amount of from about 0.01% to about 4% by weight, preferably from about 0.05% to about 3% by weight, and most preferably from about 0.05% to about 2% by weight, relative to the total weight of the composition.

In one embodiment, the compositions of the present invention further comprise at least one neutralizing agent selected from organic amines, alkali metal hydroxides, alkali earth metal hydroxides, alkali metal carbonates, alkali metal phosphates, and mixtures thereof, and preferably selected from aminomethyl propanol, sodium hydroxide, potassium hydroxide, lithium hydroxide, aminomethyl propanediol, triisopropanol amine, dimethylstearylamine, dimethyl/tallowamine, lysine, ornithine, arginine, monoethanolamine, triethanolamine, calcium hydroxide, calcium bicarbonate, and mixtures thereof.

In one embodiment, the pH of the compositions of the present invention ranges from about pH 2.5 to about 6.5, or from about pH 3 to about 6, or from about pH 3 to about 5.2, such as from about pH 3 to about 5, or preferably from about pH 3 to about 4.8, or more preferably from about pH 3 to about 4.5, or even more preferably from about pH 3 to about 4, including all ranges and sub ranges therebetween.

In one embodiment, the compositions of the present invention further comprise at least one additional component selected from organic solvents, silicones, plasticizers, opacifiers, plant/vegetable oils, hydrocarbons, lower alkanes, fragrance, preservatives, pH adjusters, plant extracts, salts, vitamins, sunscreens, colorants, and mixtures thereof In one embodiment, the present invention is directed to a hair cosmetic composition comprising:

a) at least one anionic surfactant selected from sulfate surfactants, preferably from sodium laureth sulfate, sodium lauryl sulfate, and mixtures thereof and present in an amount of from about 8% to about 15% by weight;

b) at least one amphoteric surfactant selected from (C8-C20)alkylbetaines, preferably from coco betaine, cocamidopropylbetaine, cocoamphoacetate, cocoamphodiacetate, and their salts, and mixtures thereof and present in an amount of from about 1% to about 5% by weight;

c) at least one thiol-based compound selected from thiolactic acid, thiolactic acid derivatives, their salts, and mixtures thereof and present in an amount of from about 0.8% to about 10% by weight;

d) at least one thickening agent selected from hydroxyethylcellulose (also known as HEC), hydroxymethylcellulose, methylhydroxyethylcellulose, hydroxypropylcellulose (also known as HPC), hydroxybutylcellulose, hydroxyethylmethylcellulose (also known as methyl hydroxyethylcellulose) and hydroxypropylmethylcellulose (also known as HPMC), cetyl hydroxyethylcellulose, hydroxypropyl guar gums, acrylate/C10 C30 alkyl acrylate copolymers, carbomers, polyacrylates, potato starch modified, and mixtures thereof and present in an amount of from about 0.1% to about 0.6% by weight;

e) at least one nonionic surfactant selected from cetyl alcohol, stearyl alcohol, cetearyl alcohol (mixture of cetyl alcohol and stearyl alcohol), isostearyl alcohol, PPG-5-Ceteth-10 phosphate, Oleth-3 phosphate, Oleth-10 phosphate, Ceteth-10 phosphate, laureth-7, laureth-9, trideceth-10, trideceth-12, C12-13 pareth-3, C12-13 pareth-23, C11-15 pareth-7, PPG-5 ceteth-20, PEG-55 Propylene Glycol Oleate, glycereth-26, decyl glucoside, cetearyl glucoside, decyl lauryl glucoside, stearyl glucoside, coco-glucoside, cocamide MIPA, and mixtures thereof;

f) water;

g) optionally, at least one cationic conditioning polymer; and h) optionally, at least one neutralizing agent;

wherein the pH of the composition ranges from about pH 3 to about 4; and.

all weights being relative to the total weight of the cosmetic composition.

In one embodiment, the present invention is directed to a hair cosmetic composition comprising:

a) at least one anionic surfactant selected from sulfonate surfactants, carboxylic (carboxylate) surfactants, and mixtures thereof, and preferably from sodium lauroyl sarcosinate, sodium lauryl sulfoacetate, sodium isethionate, sodium cocoyl isethionate, disodium laureth sulfosuccinate, sodium lauroyl methyl isethionate, and mixtures thereof and present in an amount of from about 8% to about 15% by weight;

b) at least one amphoteric surfactant selected from (C8-C20)alkylbetaines, (C8-C20)alkylamido (C1-C6)alkylbetaines, sulfobetaines, (C8-C20)alkylsulfobetaines, (C8-C20)alkylamido(C1-C6)alkylsulfobetaines, (C8-C20) alkylamphoacetate, (C8-C20)alkylamphodiacetate, and their salts, and mixtures thereof, preferably from coco betaine, cocamidopropylbetaine, cocoamphoacetate, cocoamphodiacetate, and their salts, and mixtures thereof, and present in an amount of from about 1% to about 5% by weight;

c) at least one thiol-based compound selected from thiolactic acid, thiolactic acid derivatives, their salts, and mixtures thereof and present in an amount of from about 0.8% to about 10% by weight;

d) at least one thickening agent selected from hydroxyethylcellulose (also known as HEC), hydroxymethylcellulose, methylhydroxyethylcellulose, hydroxypropylcellulose (also known as HPC), hydroxybutylcellulose, hydroxyethylmethylcellulose (also known as methyl hydroxyethylcellulose) and hydroxypropylmethylcellulose (also known as HPMC), cetyl hydroxyethylcellulose, hydroxypropyl guar gums, acrylate/C10 C30 alkyl acrylate copolymers, carbomers, polyacrylates, potato starch modified, and mixtures thereof and present in an amount of from about 0.1% to about 0.6% by weight;

e) at least one nonionic surfactant selected from cetyl alcohol, stearyl alcohol, cetearyl alcohol (mixture of cetyl alcohol and stearyl alcohol), isostearyl alcohol, PPG-5-Ceteth-10 phosphate, Oleth-3 phosphate, Oleth-10 phosphate, Ceteth-10 phosphate, laureth-7, laureth-9, trideceth-10, trideceth-12, C12-13 pareth-3, C12-13 pareth-23, C11-15 pareth-7, PPG-5 ceteth-20, PEG-55 Propylene Glycol Oleate, glycereth-26, decyl glucoside, cetearyl glucoside, decyl lauryl glucoside, stearyl glucoside, coco-glucoside, cocamide MIPA, and mixtures thereof;

f) water;

g) optionally, at least one cationic conditioning polymer; and h) optionally, at least one neutralizing agent;

wherein the pH of the composition ranges from about pH 3 to about 5; and all weights being relative to the total weight of the cosmetic composition.

In one embodiment of the present invention, the hair cosmetic composition in any one of the compositions described above comprises a cationic conditioning polymer preferably selected from polyquaternium-7, polyquaternium-10, guar hydroxypropyltrimonium chloride, and mixtures thereof.

In one embodiment of the present invention, the hair cosmetic composition is substantially free of anionic surfactants selected from sulfate surfactants.

In one embodiment of the present invention, the hair cosmetic composition is a cleansing or shampoo composition.

In one embodiment, the present invention is directed to a method of treating hair, the method a treatment cycle involving the steps of:

a) optionally, washing/rinsing the hair with a shampoo having a neutral pH and/or rinsing the hair with water, followed by allowing the hair to air dry, while optionally applying a smoothing action on the hair;

b) applying the composition onto the hair;

c) allowing the composition to remain on the hair for a period of time ranging from about 1 to about 10 minutes or from about 1 to about 5 minutes;

d) rinsing the hair with water;

e) drying the hair at a temperature ranging from room temperature up to about 100° C., while optionally applying a smoothing action on the hair;

f) passing a flat iron over the hair swatch at least once; and g) washing/rinsing the hair with a shampoo having a neutral pH and/or rinsing the hair with water, followed by allowing the hair to air dry, while optionally applying a smoothing action on the hair.

In accordance with the present invention, Applicants have surprisingly and unexpectedly discovered that the above-described compositions which contain thiolactic acid in combination with certain surfactants effectively clean the hair, produce good foaming properties, and at the same time, provide other hair care benefits to hair fibers such as straightening or texlaxing effects, volume reduction, frizz control, curl reduction, manageability, discipline, cosmeticity, and smooth feel.

It was also surprisingly and unexpectedly discovered that the application of the compositions of the present invention when used in combination with the processes of the present invention, results in effectively cleansed hair and imparts/improves the cosmetic properties of hair fibers, in particular human hair fibers such as the hair, for example, in terms of manageability, straightening or texlaxing effects, curl reduction, volume reduction, frizz control, manageability, discipline, cosmeticity, and smooth feel.

The compositions described above may be used on any type of hair, for example, light or dark hair, straight or curly, natural hair, or hair that has undergone a cosmetic treatment such as permanent waving, dyeing, bleaching, straightening or relaxing.

In a preferred embodiment, the composition of the present invention is applied on curly, embrittled, and/or damaged hair.

Other subjects and characteristics, aspects and advantages of the invention will emerge even more clearly on reading the description and the example that follows.

Anionic Surfactant

The at least one anionic surfactant of the present invention may be chosen from sulfate surfactants, sulfonate surfactants, carboxylic (or carboxylate) surfactants, and mixtures thereof.

The term "anionic surfactant" means a surfactant comprising, as ionic or ionizable groups, only anionic groups.

In the present description, a species is termed as being "anionic" when it bears at least one permanent negative charge or when it can be ionized as a negatively charged species, under the conditions of use of the composition of the invention (for example the medium or the pH) and not comprising any cationic charge.

It is understood in the present description that:
carboxylate anionic surfactants comprise at least one carboxylic or carboxylate function (~COOH or —COO—) and may optionally also comprise one or more sulfate and/or sulfonate functions;
the sulfonate anionic surfactants comprise at least one sulfonate function (—SO$_3$H or —SO$_3$—) and may optionally also comprise one or more sulfate functions, but do not comprise any carboxylate functions; and
the sulfate anionic surfactants comprise at least one sulfate function but do not comprise any carboxylate or sulfonate functions.

The carboxylic anionic surfactants that may be used thus comprise at least one carboxylic or carboxylate function (~COOH or —COO—).

They may be chosen from the following compounds:
acylglycinates, acyllactylates, acylsarcosinates, acylglutamates; alkyl-D-galactosideuronic acids, alkyl ether carboxylic acids, alkyl(C$_{6-30}$ aryl) ether carboxylic acids, alkylamido ether carboxylic acids; and also the salts of these compounds;
the alkyl and/or acyl groups of these compounds comprising from 6 to 30 carbon atoms, especially from 12 to 28, better still from 14 to 24 or even from 16 to 22 carbon atoms; the aryl group preferably denoting a phenyl or benzyl group;
these compounds possibly being polyoxyalkylenated, especially polyoxyethylenated, and then preferably comprising from 1 to 50 ethylene oxide units and better still from 2 to 10 ethylene oxide units.

Use may also be made of the C$_6$-C$_{24}$ alkyl monoesters of polyglycoside-polycarboxylic acids, such as C$_6$-C$_{24}$ alkyl polyglycoside-citrates, C$_6$-C$_{24}$ alkyl polyglycoside-tartrates and C$_6$-C$_{24}$ alkyl polyglycoside-sulfosuccinates, and salts thereof.

Among the above carboxylic surfactants, mention may be made most particularly of polyoxyalkylenated alkyl(amido) ether carboxylic acids and salts thereof, in particular those comprising from 2 to 50 alkylene oxide and in particular ethylene oxide groups, such as the compounds sold by the company Kao under the name Akypo.

The polyoxyalkylenated alkyl (amido) ether carboxylic acids that may be used are preferably chosen from those of formula (1):

$$R_1—(OC_2H_4)_n—OCH_2COOA \quad (1)$$

in which:
R$_1$ represents a linear or branched C$_6$-C$_{24}$ alkyl or alkenyl radical, an alkyl(C8-C9)phenyl radical, a radical R$_2$CONH—CH$_2$—CH$_2$— with R$_2$ denoting a linear or branched C$_9$-C$_{21}$ alkyl or alkenyl radical,
preferably, R$_1$ is a C$_8$-C$_{20}$ and preferably C$_8$-C$_{18}$ alkyl radical, and aryl preferably denotes phenyl,
n is an integer or decimal number (average value) ranging from 2 to 24 and preferably from 2 to 10,
A denotes H, ammonium, Na, K, Li, Mg or a monoethanolamine or triethanola-mine residue.

It is also possible to use mixtures of compounds of formula (1), in particular mixtures of compounds containing different groups R1.

The polyoxyalkylenatedalkyl(amido) ether carboxylic acids that are particularly preferred are those of formula (1) in which:
R1 denotes a C$_{12}$-C$_{14}$ alkyl, cocoyl, oleyl, nonylphenyl or octylphenyl radical, A denotes a hydrogen or sodium atom, and
n varies from 2 to 20 and preferably from 2 to 10.

Even more preferentially, use is made of compounds of formula (1) in which R denotes a C$_{12}$ alkyl radical, A denotes a hydrogen or sodium atom and n ranges from 2 to 10.

Preferentially, the carboxylic anionic surfactants are chosen, alone or as a mixture, from:
acylglutamates, especially of C$_6$-C$_{24}$ or even C$_{12}$-C$_{20}$, such as stearoylgluta-mates, and in particular disodium stearoylglutamate;
acylsarcosinates, especially of C$_6$-C$_{24}$ or even C$_{12}$-C$_{20}$, such as palmitoylsar-cosinates, and in particular sodium palmitoylsarcosinate;
acyllactylates, especially of C$_{12}$-C$_{28}$ or even C$_{14}$-C$_{24}$, such as behenoyllac-tylates, and in particular sodium behenoyllactylate;
C$_6$-C$_{24}$ and especially C$_{12}$-C$_{20}$ acylglycinates;
(C$_6$-C$_{24}$)alkyl ether carboxylates and especially (C$_{12}$-C$_{20}$) alkyl ether carbox-ylates;
polyoxyalkylenated (C$_6$-C$_{24}$)alkyl(amido) ether carboxylic acids, in particular those comprising from 2 to 50 ethylene oxide groups;
in particular in the form of alkali metal or alkaline-earth metal, ammonium or amino alcohol salts.

The sulfonate anionic surfactants that may be used comprise at least one sulfonate function (—SO$_3$H or —SO$_3$—).

They may be chosen from the following compounds:
alkylsulfonates, alkyla-midesulfonates, alkylarylsulfonates, α-olefinsulfonates, paraffin sulfonates, alkylsulfosuccinates, alkyl ether sulfosuccinates, alkylamidesulfosuccinates, alkyl-sulfoacetates, N-acyltaurates, acylisethionates; alkylsulfolaurates; and also the salts of these compounds;
the alkyl groups of these compounds comprising from 6 to 30 carbon atoms, especially from 12 to 28, better still from 14 to 24 or even from 16 to 22 carbon atoms; the aryl group preferably denoting a phenyl or benzyl group;
these compounds possibly being polyoxyalkylenated, especially polyoxyethylenated, and then preferably comprising from 1 to 50 ethylene oxide units and better still from 2 to 10 ethylene oxide units.

Preferentially, the sulfonate anionic surfactants are chosen, alone or as a mixture, from:
C$_6$-C$_{24}$ and especially C$_{12}$-C$_{20}$ alkylsulfosuccinates, especially laurylsulfosuccinates;
C$_6$-C$_{24}$ and especially C$_{12}$-C$_{20}$ alkyl ether sulfosuccinates;
(C$_6$-C$_{24}$)acylisethionates and preferably (C$_{12}$-C$_{18}$)acyli-sethionates,
in particular in the form of alkali metal or alkaline-earth metal, ammonium or amino alcohol salts.

The sulfate anionic surfactants that may be used comprise at least one sulfate function (—OSO$_3$H or —OSO$_3$—).

They may be chosen from the following compounds:
alkyl sulfates, alkyl ether sulfates, alkylamido ether sulfates, alkylaryl polyether sulfates, monoglyceride sulfates; and also the salts of these compounds;
the alkyl groups of these compounds comprising from 6 to 30 carbon atoms, especially from 12 to 28, better still from 14 to 24 or even from 16 to 22 carbon atoms; the aryl group preferably denoting a phenyl or benzyl group;
these compounds possibly being polyoxyalkylenated, especially polyoxyethylenated, and then preferably comprising from 1 to 50 ethylene oxide units and better still from 2 to 10 ethylene oxide units.

Preferentially, the sulfate anionic surfactants are chosen, alone or as a mixture, from:
- alkyl sulfates, especially of $C_6$-$C_{24}$ or even $C_{12}$-$C_{20}$,
- alkyl ether sulfates, especially of $C_6$-$C_{24}$ or even $C_{12}$-$C_{20}$, preferably comprising from 2 to 20 ethylene oxide units;
- in particular in the form of alkali metal or alkaline-earth metal, ammonium or amino alcohol salts.

When the anionic surfactant is in salt form, the said salt may be chosen from alkali metal salts, such as the sodium or potassium salt, ammonium salts, amine salts and in particular amino alcohol salts, and alkaline-earth metal salts, such as the magnesium salt.

Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Preferentially, the anionic surfactants are chosen, alone or as a mixture, from:
- $C_6$-$C_{24}$ and especially $C_{12}$-$C_{20}$ alkyl sulfates;
- $C_6$-$C_{24}$ and especially $C_{12}$-$C_{20}$ alkyl ether sulfates; preferably comprising from 2 to 20 ethylene oxide units;
- $C_6$-$C_{24}$ and especially $C_{12}$-$C_{20}$ alkylsulfosuccinates, especially laurylsulfosuccinates;
- $C_6$-$C_{24}$ and especially $C_{12}$-$C_{20}$ alkyl ether sulfosuccinates;
- ($C_6$-$C_{24}$)acylisethionates and preferably ($C_{12}$-$C_{18}$)acylisethionates;
- $C_6$-$C_{24}$ and especially $C_{12}$-$C_{20}$ acylsarcosinates; especially palmitoylsar-cosinates;
- ($C_6$-$C_{24}$)alkyl ether carboxylates, preferably ($C_{12}$-$C_{20}$) alkyl ether carboxylates;
- polyoxyalkylenated ($C_6$-$C_{24}$)alkyl(amido) ether carboxylic acids and salts there-of, in particular those comprising from 2 to 50 alkylene oxide and in particular ethylene oxide groups;
- $C_6$-$C_{24}$ and especially $C_{12}$-$C_{20}$ acylglutamates;
- $C_6$-$C_{24}$ and especially $C_{12}$-$C_{20}$ acylglycinates;
- in particular in the form of alkali metal or alkaline-earth metal, ammonium or amino alcohol salts.

In some embodiments, the at least one anionic surfactant of the present invention is chosen from sulfate surfactants.

In certain embodiments, the at least one anionic surfactant of the present invention is preferably chosen from sodium lauryl sulfate, sodium laureth sulfate, and mixtures thereof.

In an embodiment, the at least one anionic surfactant of the present invention comprises sodium lauryl sulfate and sodium laureth sulfate.

In some embodiments, the at least one anionic surfactant of the present invention is chosen from sulfonate surfactants.

In certain embodiments, the at least one anionic surfactant of the present invention is preferably chosen from sodium lauryl sulfoacetate, sodium isethionate, sodium cocoyl isethionate, disodium laureth sulfosuccinate, sodium lauroyl methyl isethionate, and mixtures thereof.

In some embodiments, the at least one anionic surfactant of the present invention is chosen from carboxylic (carboxylate) surfactants.

In one embodiment of the present invention, the at least one anionic surfactant is selected from sodium lauroyl sarcosinate.

In one embodiment of the present invention, the at least one anionic surfactant is not a sulfate surfactant and is chosen sulfonate surfactants including sodium lauroyl sarcosinate, sodium lauryl sulfoacetate, sodium isethionate, sodium cocoyl isethionate, disodium laureth sulfosuccinate, sodium lauroyl methyl isethionate, and mixtures thereof.

In one embodiment of the present invention, the at least one anionic surfactant comprises sulfate surfactants, sulfonate surfactants, and carboxylic (carboxylate) surfactants.

In one embodiment of the present invention, the composition is substantially free of anionic surfactants selected from sulfate surfactants.

The term "substantially free" as used herein means that there is less than 1% by weight, of anionic surfactants added to the composition, and the term does not refer to or include anionic surfactants that may be present in raw materials as commercially available from suppliers.

The at least one anionic surfactant is present in the compositions of the invention in a total amount of from about 5% to about 20% by weight, such as from about 6% to about 18% by weight, or preferably from about 8% to about 15% by weight, relative to the total weight of the composition by weight, including all ranges and sub ranges there between.

In a particular embodiment, the total amount of anionic surfactants is at about 6%, 6.25%, 6.5%, 6.75%, 7%, 7.25%, 7.5%, 7.75%, 8%, 8.25%, 8.5 8.75%, 9%, 9.25%, 9.5%, 9.75%, 10%, 10.25%, 10.5%, 10.75%, 11%, 11.25%, 11.5%, 11.75%, 12%, 12.3%, 12.5%, 12.75%, 13%, 13.25%, 13.5%, 13.75%, 14%, 14.25%, 14.5%, 14.75%, or 15% by weight, relative to the total weight of the composition.

Amphoteric Surfactant

The amphoteric surfactants of the present invention may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Mention may be made in particular of ($C_8$-$C_{20}$)alkylbetaines, ($C_8$-$C_{20}$)alkylamido ($C_1$-$C_6$)alkylbetaines, sulfobetaines, ($C_8$-$C_{20}$)alkylsulfobetaines, ($C_8$-$C_{20}$)alkylamido ($C_1$-$C_6$)alkylsulfobetaines, ($C_8$-$C_{20}$)alkylamphoacetate, ($C_8$-$C_{20}$)alkylamphodiacetate, and mixtures thereof.

Among the optionally quaternized secondary or tertiary aliphatic amine derivatives that may be used, mention may also be made of the products of respective structures (A1) and (A2) below:

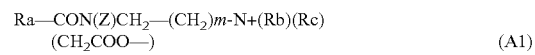

$$\text{Ra—CON(Z)CH}_2\text{—(CH}_2)m\text{-N+(Rb)(Rc)} \quad (A1)$$
$$(\text{CH}_2\text{COO—})$$

in which:
Ra represents a $C_{10}$-$C_{30}$ alkyl or alkenyl group derived from an acid Ra—COOH preferably present in hydrolysed coconut oil, a heptyl group, a nonyl group or an undecyl group,
Rb represents a β-hydroxyethyl group,
Rc represents a carboxymethyl group;
m is equal to 0, 1 or 2,
Z represents a hydrogen atom or a hydroxyethyl or carboxymethyl group;

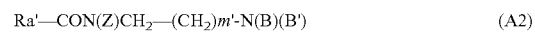

$$\text{Ra'—CON(Z)CH}_2\text{—(CH}_2)m'\text{-N(B)(B')} \quad (A2)$$

in which:
B represents —$CH_2CH_2OX'$, with $X'$ representing —$CH_2$—COOH, $CH_2$—COOZ', $CH_2CH_2$—COOH, —$CH_2CH_2$—COOZ', or a hydrogen atom, B' represents —(CH$_2$)z-Y', with z=1 or 2, and Y' representing COOH, COOZ', CH$_2$—CHOH—SO$_3$H or —CH$_2$—CHOH—SO$_3$Z', m' is equal to 0, 1 or 2, Z represents a hydrogen atom or a hydroxyethyl or carboxymethyl group, Z' represents an ion resulting from an alkali or alkaline-earth metal, such as sodium, potassium or magnesium; an ammonium ion; or an ion resulting from an organic amine and in particular from an amino alcohol, such as monoethanola-mine, diethanolamine and triethanolamine, monoisopropanolamine, diisopropa-nolamine or triisopropanolamine, 2-amino-2-methyl-1-propanol, 2-amino-2-methyl-1,3-propanediol and tris(hydroxymethyl) aminomethane, Ra' represents a C$_{10}$-C$_{30}$ alkyl or alkenyl group of an acid Ra'COOH preferably pre-sent in hydrolysed linseed oil or coconut oil, an alkyl group, in particular a C$_{17}$ alkyl group, and its iso form, or an unsaturated C$_{17}$ group.

Among the compounds corresponding to formula (A2) in which X' represents an hydrogen atom, mention may be made of compounds classified in the CTFA dictionary, under the names sodium cocoamphoacetate, sodium lauroamphoacetate, sodium caproamphoacetate and sodium capryloamphoacetate.

Other compounds corresponding to formula (A2) are disodium cocoamphodiace-tate, disodium lauroamphodiacetate, disodium caproamphodiacetate, disodium capryloamphodiacetate, disodium cocoamphodipropionate, disodium lauroam-phodipropionate, disodium caproamphodipropionate, disodium capryloamphodi-propionate, lauroamphodipropionic acid and cocoamphodipropionic acid.

Examples that may be mentioned include the cocoamphodiacetate sold by the company Rhodia under the trade name Miranol® C2M Concentrate, the sodium cocoamphoacetate sold under the trade name Miranol Ultra C 32 and the product sold by the company Chimex under the trade name CHIMEXANE HA.

Use may also be made of the compounds of formula (A3):

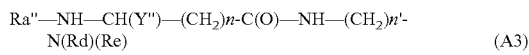

Ra"—NH—CH(Y")—(CH$_2$)n-C(O)—NH—(CH$_2$)n'-N(Rd)(Re)    (A3)

in which:

Ra" represents a C10-C30 alkyl or alkenyl group of an acid Ra"'—C(O)OH preferably present in hydrolysed linseed oil or coconut oil;

Y" represents the group —C(O)OH, —C(O)OZ", —CH$_2$—CH(OH)—SO$_3$H or the group CH$_2$—CH(OH)—SO$_3$—Z", with Z" representing a cationic counterion resulting from an alkali metal or alkaline-earth metal, such as sodium, an ammonium ion or an ion resulting from an organic amine;

Rd and Re represent, independently of each other, a C$_1$-C$_4$ alkyl or hydroxyalkyl radical; and n and n' denote, independently of each other, an integer ranging from 1 to 3.

Among the compounds corresponding to formula (A3), mention may in particular be made of the compound classified in the CTFA dictionary under the name sodi-um diethylaminopropylcocoaspartamide, such as the one sold by the company Chimex under the name CHIMEXANE HB.

Preferably, the amphoteric surfactants are chosen from (C$_8$-C$_{20}$)alkylbetaines, (C$_8$-C$_{20}$)alkylamido(C$_1$-C$_6$)alkylbetaines, (C$_8$-C$_{20}$)alkylamphoacetates and (C$_8$-C$_{20}$)alkylamphodiacetates, and mixtures thereof.

In some embodiments, the at least one amphoteric surfactant of the present invention is chosen from (C$_8$-C$_{20}$)alkylbetaines, (C$_8$-C$_{20}$)alkylamido (C$_1$-C$_6$)alkylbetaines, (C$_8$-C$_{20}$)alkylamphoacetate, (C$_8$-C$_{20}$)alkylamphodiacetate, and their salts, and mixtures thereof.

Preferably, the amphoteric surfactants are chosen from (C$_8$-C$_{20}$)alkylbetaines such as the one known under the INCI names coco-betaine, (C$_8$-C$_{20}$)alkylamido(C$_1$-C$_6$)alkylbetaines such as the one known under the INCI name cocamidopropylbetaine, and mixtures thereof. Even more preferentially, the amphoteric surfactant is coco-betaine.

In one embodiment of the present invention, the at least one amphoteric surfactant is selected from coco-betaine, cocamidopropylbetaine, sodium cocoamphoacetate, disodium cocoamphodiacetate, and mixtures thereof.

In one embodiment of the present invention, the amount of amphoteric surfactants ranges from about 0.1% to about 10% by weight, preferably from about 0.5% to about 8% by weight, more preferably from about 0.8% to about 6% by weight, and even more preferably from about 1% to about 5% by weight, relative to the total weight of the composition, including all ranges and subranges therebetween.

In a particular embodiment, the amount of the at least one amphoteric surfactant is at about 1%, 1.25%, 1.5%, 1.55%, 1.6%, 1.65%, 1.7%, 1.75%, 1.8%, 1.85%, 1.9%, 1.95%, 2%, 2.05%, 2.1%, 2.15%, 2.2%, 2.25%, 2.3%, 2.35%, 2.4%, 2.45%, 2.5%, 2.55%, 2.6%, 2.65%, 2.7%, 2.75%, 2.8%, 2.85%, 2.9%, 3.0%, 3.25%, 3.5%, 3.75%, 4%, 4.25%, 4.5%, 4.75%, or 5% by weight, relative to the total weight of the composition.

Thiol-Based Compounds

The present invention employs at least one thiol-based compound selected from thiolactic acid, thiolactic acid derivatives, their salts, and mixtures thereof.

In one embodiment, the thiol-based compound used in the composition of the invention can be selected from thiolactic acid and/or one or more alkali metal or alkaline earth metal salts thereof.

In one embodiment, the thiol-based compound used in the composition of the invention can be selected from of thiolactic acid, sodium thiolactic acid (sodium thiolactate), potassium thiolactic acid (potassium thiolactate), magnesium thiolactic acid (magnesium thiolactate), strontium thiolactic acid (strontium thiolactate), ammonium thiolactate, and mixtures thereof.

In one embodiment, the thiol-based compound used in the composition of the invention can be selected from thiolactic acid, thiolactic acid derivatives such as glycerol monothiolactate, thiolactic acid ammonium salts such as ammonium thiolactate, and mixtures thereof.

The at least one thiol-based compound of the present disclosure can be used in combination with other thiol-based compounds selected from thioglycolic acid, cysteine, cysteamine, homocystine, glutathione, thioglycerol, thiomalic acid, 2-mercaptopropionic acid, 3-mercaptopropionic acid, thio diglycol, 2-mercaptoethanol, dithiothreitol, thioxanthine, thiosalicylic acid, thiopropionic acid, lipoic acid, N-acetylcysteine, their salts thereof, and mixtures thereof.

The at least one thiol-based compound of the present disclosure can be also be used in combination with non-thiol based compounds such as alkali metal, alkaline-earth metal sulfites, hydrides or phosphines, and mixtures thereof.

In certain embodiments, the thiol-based compound used in the composition of the invention is thiolactic acid.

The at least one thiol-based compound can be employed in the compositions of the present invention in an amount of from about 0.5% to about 15% by weight, preferably from about 0.6% to about 14% by weight, more preferably from about 7% to about 12% by weight, more preferably from about 0.8% to about 10% by weight, or from about 1% to about 8% by weight, relative to the total weight of the composition, including all ranges and subranges therebetween.

In certain embodiments, the at least one thiol-based compound is selected from thiolactic acid and is employed in the composition of the present invention in an amount of about 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.5%, 10%, 10.5%, 11%, 11.5%, 12%, 13%, 14% by weight, relative to the total weight of the composition.

Thickening Agents

The compositions according to the present disclosure may further comprise at least one thickening agent. Thickening agents are generally used to modify the viscosity and/or rheology of the composition. As used herein, the term "thickening agent" means compounds which, by their presence, increase the viscosity of the composition into which they are introduced by at least 20 cps, such as by at least 50 cps, at 25° C. and at a shear rate of 1 s-1. The viscosity may be measured using a cone/plate viscometer, a Haake R600 rheometer, or the like.

The thickening agent may be referred to interchangeably herein as thickener or rheology modifier. Thickening agents are also sometimes referred to as gellifying agents and/or viscosity modifying agents.

In certain embodiments, the thickening agent may be chosen from those conventionally used in cosmetics, such as polymers of natural origin and synthetic polymers, for example, nonionic, anionic, cationic, amphiphilic, or amphoteric polymers, and other known rheology modifiers, such as cellulose-based thickeners.

In certain embodiments, the thickening agents can be an anionic thickening agent.

The anionic thickening agents may be chosen from hydrophilic thickeners. As used herein, the term "hydrophilic thickener" is meant to indicate that the thickening agent is soluble or dispersible in water. Non-limiting examples of hydrophilic thickeners include homopolymers or copolymers of acrylic or methacrylic acids or the salts thereof and the esters thereof, such as those sold under the tradenames Versicol F® or Versicol K® by the company Allied Colloid, or under the tradename Ultrahold 8® by the company Ciba-Geigy; polyacrylates and polymethacrylates such as copolymers of (meth)acrylic acid, copolymers of (meth) acrylic acid, methylacrylate and dimethyl meta-isopropenyl benzyl isocyanate of ethoxylated alcohols such as methylacrylate and dimethyl meta-isopropenyl benzyl isocyanate of ethoxylated alcohol (INCI name: Polyacrylate-3) sold under the tradename Viscophobe® DB 1000 from The Dow Chemical Company, those sold under the tradenames Lubrajel and Norgel by the company Guardian, or under the tradename Hispajel by the company Hispano Chimica; and polyacrylic acids of Synthalen® K type, copolymers of acrylic acid and of acrylamide sold in the form of the sodium salt thereof, such as those sold under the tradenames Reten® by Hercules, sodium polymethacrylate such as those sold under the tradename Darvan® 7 by the company Vanderbilt, and the sodium salts of polyhydroxycarboxylic acids such as those sold under the tradename Hydagen F® by the company Henkel, polyacrylic acid/alkyl acrylate copolymers of Pemulen™ type, associative polymers, for instance PEG-150/stearyl alcohol/SMDI copolymer such those as sold under the tradename ACULYN™ 46 by the company Rohm & Haas, steareth-100/PEG-136/HDI copolymer such as those sold under the tradename Rheolate® FX 1100 by the company Elementis, and mixtures thereof.

As used herein, the term "copolymers" is intended to mean both copolymers obtained from two types of monomers and those obtained from more than two types of monomers, such as, for example, terpolymers obtained from three types of monomers. The chemical structure of the copolymers comprises at least one hydrophilic unit and at least one hydrophobic unit. The expression "hydrophobic unit" or "hydrophobic unit" is understood to mean a radical possessing a saturated or unsaturated and linear or branched hydrocarbon-based chain which comprises at least 8 carbon atoms, for example from 10 to 30 carbon atoms, as a further example from 12 to 30 carbon atoms, and as yet a further example from 18 to 30 carbon atoms.

In certain embodiments, the hydrophilic thickener may be chosen from anionic associative polymers. As used herein, the term "associative polymer" is intended to mean any polymer comprising in its structure at least one fatty chain and at least one hydrophilic portion.

In certain embodiments, the associative polymers may be chosen from polymers comprising at least one hydrophilic unit and at least one fatty-chain allyl ether unit; polymers in which the hydrophilic unit is constituted of an ethylenic unsaturated anionic monomer, such as a vinylcarboxylic acid, acrylic acid, methacrylic acid, or mixtures thereof; and polymers in which the fatty-chain allyl ether unit corresponds to the monomer of formula (I) below:

$$CH_2=C(R')CH_2OB_nR \quad (I)$$

in which R' is chosen from H or CH3, B is an ethyleneoxy radical, n is zero or is chosen from an integer ranging from 1 to 100, and R is a hydrocarbon-based radical chosen from alkyl, arylalkyl, aryl, alkylaryl, or cycloalkyl radicals containing from 8 to 30 carbon atoms, from 10 to 24 carbon atoms, or from 12 to 18 carbon atoms. Exemplary and non-limiting polymers of this type are described and prepared, according to an emulsion polymerization process, in patent EP 0 216 479, incorporated by reference herein.

In certain embodiments, the associative anionic polymer may be chosen from anionic polymers comprising at least one hydrophilic unit of olefinic unsaturated carboxylic acid type, and at least one hydrophobic unit exclusively of (C10 C30)alkyl ester of unsaturated carboxylic acid type.

In certain embodiments, the at least one thickening agent is chosen from copolymers resulting from the polymerization of at least one monomer (a) chosen from carboxylic acids possessing α,β-ethylenically unsaturated groups or their esters, with at least one monomer (b) possessing ethylenically unsaturated groups and comprising a hydrophobic group. Such copolymers may exhibit emulsifying properties.

As used herein, the term "copolymers" is intended to mean both copolymers obtained from two types of monomers and those obtained from more than two types of monomers, such as, for example, terpolymers obtained from three types of monomers. The chemical structure of the copolymers comprises at least one hydrophilic unit and at least one hydrophobic unit. The expression "hydrophobic unit" or "hydrophobic unit" is understood to mean a radical possessing a saturated or unsaturated and linear or branched hydrocarbon-based chain which comprises at least 8 carbon atoms, for example from 10 to 30 carbon atoms, as a further example from 12 to 30 carbon atoms, and as yet a further example from 18 to 30 carbon atoms.

In certain embodiments, the thickening copolymer may be chosen from the copolymers resulting from the polymerization of:

(1) at least one monomer of formula (II):

$$CH2=CH(R1)COOH \quad (II)$$

wherein R1 is chosen from H, CH3, or C2H5, providing acrylic acid, methacrylic acid, or ethacrylic acid monomers, and (2) at least one monomer of (C10 C30)alkyl ester of unsaturated carboxylic acid type corresponding to the monomer of formula (III):

$$CH2=CH(R2)COOR3 \quad (III)$$

wherein R2 is chosen from H, CH3, or C2H5, providing acrylate, methacrylate or ethacrylate units, and R3 denotes a C10 C30 alkyl radical, such as a C12 C22 alkyl radical.

In certain embodiments, the (C10 C30)alkyl esters of unsaturated carboxylic acids may be chosen from lauryl acrylate, stearyl acrylate, decyl acrylate, isodecyl acrylate, dodecyl acrylate or the corresponding methacrylates, such as lauryl methacrylate, stearyl methacrylate, decyl methacrylate, isodecyl methacrylate or dodecyl methacrylate, or mixtures thereof.

In certain embodiments, the crosslinked thickening polymer may be chosen from polymers resulting from the polymerization of a mixture of monomers comprising:

(1) acrylic acid, (2) an ester of formula (III) described above, in which R2 is chosen from H or CH3, R3 denotes an alkyl radical having from 12 to 22 carbon atoms, and (3) a crosslinking agent, which is a known copolymerizable polyethylenic unsaturated monomer, such as diallyl phthalate, allyl (meth)acrylate, divinylbenzene, (poly)ethylene glycol dimethacrylate and methylenebisacrylamide.

In various embodiments, the crosslinked thickening polymer may comprise from about 60% to about 95% by weight of acrylic acid (hydrophilic unit), from about 4% to about 40% by weight of C10 C30 alkyl acrylate (hydrophobic unit), and from about 0% to about 6% by weight of crosslinking polymerizable monomer. In further embodiments, the crosslinked thickening polymer may comprise from about 96% to about 98% by weight of acrylic acid (hydrophilic unit), from about 1% to about 4% by weight of C10 C30 alkyl acrylate (hydrophobic unit), and from about 0.1% to 0.6% by weight of crosslinking polymerizable monomer, such as those described above.

In some embodiments, the crosslinked thickening polymer may be chosen from acrylate/C10 C30 alkyl acrylate copolymers (INCI name: Acrylates/C10-30 Alkyl Acrylate Crosspolymer), such as the products sold under the tradenames Pemulen™ TR1, Pemulen™ TR2, Carbopol® 1382 and Carbopol® EDT 2020 by the company Lubrizol.

The anionic thickening agent may also be known as rheology modifiers such as acrylate- or acrylic-based polymers, carbomers, crosslinked homopolymers of acrylic acid or of acrylamidopropane-sulfonic acid, and crosslinked copolymers of (meth)acrylic acid and/or (C1-C6)alkyl esters.

In an embodiment, the anionic thickening agent is chosen from polyacrylate-3, commercially known under the trade name of Viscophobe DB-100 and sold by The Dow Chemical Company, carbomers, commercially known under the trade name of Carbopol polymers and sold by Lubrizol Advance Materials, Inc, acrylates/C10-30 alkyl acrylate crosspolymers, commercially known the trade names of Pemulen TR-1 and Pemulen TR-2 polymers and sold by Lubrizol Advance Materials, Inc, Acrylates/C10-30 Alkyl Acrylate Crosspolymer such as Carbopol® Ultrez 20 Polymer by and sold by Lubrizol Advance Materials, Inc., AMP-acrylates/allyl methacrylate copolymer, commercially known under the trade name of Fixate G-100 polymer and sold by Lubrizol Advance Materials, Inc., Polyacrylate Crosspolymer-6 such as Sepimax™ Zen by the company Seppic, and a crosslinked methacrylic acid/ethyl acrylate copolymer, also known as an acrylates copolymer in aqueous dispersion, such as the slightly cross-linked, alkali-swellable acrylate polymer known by the INCI name acrylates copolymer and sold by Lubrizol, under the tradename CARBOPOL Aqua SF-1 as an aqueous dispersion comprising about 30 percent by weight of total solids or active material.

In various embodiments, the thickening agents may be chosen from hydrophilic thickeners, for example cellulose polymers and gums, modified or unmodified carboxyvinyl polymers, such as those sold under the tradename Carbopol® (CTFA name: carbomer) by the company Goodrich, polyacrylamides, copolymers of acrylic acid and of acrylamide sold in the form of the sodium salt thereof, such as those sold under the tradenames Reten® by Hercules, and the sodium salts of polyhydroxycarboxylic acids such as those sold under the tradename Hydagen F® by the company Henkel, optionally crosslinked and/or neutralized 2-acrylamido-2-methylpropanesulphonic acid polymers and copolymers, for instance poly(2-acrylamido-2-methylpropanesulphonic acid) such as those sold under the tradename Hostacerin® AMPS (CTFA name: ammonium polyacryldimethyltauramide) by the company Clariant, crosslinked anionic copolymers of acrylamide and of AMPS, e.g. in the form of a water-in-oil emulsion, such as those sold under the tradename Sepigel™ 305 (CTFA name: Polyacrylamide/C13-14 Isoparaffin/Laureth-7) and under the tradename Simugel™ 600 (CTFA name: Acrylamide/Sodium acryloyldimethyltaurate copolymer/Isohexadecane/Polysorbate 80) by the company Seppic, polyacrylic acid/alkyl acrylate copolymers of Pemulen™ type, associative polymers, for instance PEG-150/stearyl alcohol/SMDI copolymer such those as sold under the tradename ACULYN™ 46 by the company Rohm & Haas, steareth-100/PEG-136/HDI copolymer such as those sold under the tradename Rheolate® FX 1100 by the company Elementis, and mixtures thereof.

In certain embodiments, the hydrophilic thickener may be chosen from associative polymers. As used herein, the term "associative polymer" is intended to mean any amphiphilic polymer comprising in its structure at least one fatty chain and at least one hydrophilic portion. As used herein, the term "amphiphilic polymer" means a polymer composed of hydrophilic and hydrophobic parts.

In certain embodiments, the associative polymers may be anionic, cationic, nonionic, or amphoteric. In certain embodiments, the associative polymers may be chosen from polymers comprising at least one hydrophilic unit and at least one fatty-chain allyl ether unit; polymers in which the hydrophilic unit is constituted of an ethylenic unsaturated anionic monomer, such as a vinylcarboxylic acid, acrylic acid, methacrylic acid, or mixtures thereof; and polymers in which the fatty-chain allyl ether unit corresponds to the monomer of formula (I) below:

$$CH2=C(R')CH2OBnR \quad (I)$$

in which R' is chosen from H or CH3, B is an ethyleneoxy radical, n is zero or is chosen from an integer ranging from 1 to 100, and R is a hydrocarbon-based radical chosen from alkyl, arylalkyl, aryl, alkylaryl, or cycloalkyl radicals containing from 8 to 30 carbon atoms, from 10 to 24 carbon atoms, or from 12 to 18 carbon atoms. Exemplary and non-limiting polymers of this type are described and prepared, according to an emulsion polymerization process, in patent EP 0 216 479, incorporated by reference herein.

In other embodiments, the associative cationic polymer may be chosen from quaternized cellulose derivatives and polyacrylates containing amine side groups.

In other embodiments, the non-ionic associative polymer may be chosen from celluloses modified with groups comprising at least one fatty chain, for instance hydroxyethyl celluloses modified with groups comprising at least one fatty chain, such as alkyl groups, e.g. C8-C22 alkyl groups, arylalkyl and alkylaryl groups; cetyl hydroxyethyl cellulose, also known under the tradename Natrosol® Plus (sold by the company Ashland), Bermocoll EHM 100 (sold by the company Berol Nobel), Amercell Polymer HM-1500® sold by the company Amerchol; hydroxyethylcellulose modified with a polyethylene glycol (15) nonylphenyl ether group, sold by the company Amerchol; celluloses modified with polyalkylene glycol alkylphenyl ether groups; guars such as hydroxypropyl guar, optionally modified with groups comprising at least one fatty chain such as an alkyl chain, for example Jaguar® XC-95/3 (C14 alkyl chain, sold by the company Rhodia Chimie), Esaflor HM 22 (C22 alkyl chain, sold by the company Lamberti), RE210-18 (C14 alkyl chain) and RE205-1 (C20 alkyl chain, sold by the company Rhodia Chimie); copolymers of vinylpyrrolidone and of fatty-chain hydrophobic monomers, for instance Antaron® or Ganex® V216 (vinylpyrrolidone/hexadecene copolymers), Antaron® or Ganex® V220 (vinylpyrrolidone/eicosene copolymers) sold by the company I.S.P.; copolymers of C1-C6 alkyl methacrylates, acrylates or amphiphilic monomers comprising at least one fatty chain; or copolymers of hydrophilic methacrylates, acrylates or hydrophobic monomers comprising at least one fatty chain, for instance the polyethylene glycol methacrylate/lauryl methacrylate copolymer.

Associative polyurethanes may also be chosen in various embodiments. As used herein, "associative polyurethanes" are nonionic block copolymers comprising in the chain both hydrophilic blocks usually of polyoxyethylene nature, and hydrophobic blocks that may be aliphatic sequences alone and/or cycloaliphatic and/or aromatic sequences. Associative polyurethanes comprise at least two hydrocarbon-based lipophilic chains containing from C6 to C30 carbon atoms, separated by a hydrophilic block, the hydrocarbon-based chains optionally being pendent chains or chains at the end of a hydrophilic block. For example, it is possible for one or more pendent chains to be provided. In addition, the polymer may comprise a hydrocarbon-based chain at one or both ends of a hydrophilic block. The associative polyurethanes may be arranged in triblock or multiblock form. The hydrophobic blocks may thus be at each end of the chain (for example, triblock copolymer with a hydrophilic central block) or distributed both at the ends and within the chain (for example, multiblock copolymer). These polymers may also be graft polymers or starburst polymers. In one embodiment, the associative polyurethanes may be triblock copolymers in which the hydrophilic block is a polyoxyethylene chain containing from 50 to 1000 oxyethylene groups.

In other embodiments, associative polymers of the polyurethane polyether type that may be used include the polymer C16-OE120-C16 from Servo Delden (under the tradename SER AD FX1100), which is a molecule containing a urethane function and having a weight-average molecular weight of 1300, OE being an oxyethylene unit; Nuvis® FX 1100 (European and US INCI name "Steareth-100/PEG-136/HMDI Copolymer" sold by the company Elementis Specialties); Acrysol RM 184® (sold by the company Rohm and Haas); Elfacos® T210® (C12-C14 alkyl chain); Elfacos® T212® (C18 alkyl chain) sold by the company Akzo; Rheolate® 205 containing a urea function, sold by the company Rheox; RHEOLATE® 208 or 204, or RHEOLATE® FX1100 sold by the company Elementis; or DW 1206B sold by the company Rohm & Haas containing a C20 alkyl chain with a urethane bond, sold at a solids content of 20% in water.

In further embodiments, solutions or dispersions of these polymers, especially in water or in aqueous-alcoholic medium, may be chosen. Examples of such polymers include SER AD FX1010, SER AD FX1035, and SER AD 1070 from the company Servo Delden, and Rheolate® 255, Rheolate® 278, and Rheolate® 244 sold by Rheox. Further examples include the products Aculyn™ 46, DW 1206F, and DW 1206J, Acrysol RM 184 or Acrysol 44 from the company Rohm & Haas, and Borchi® Gel LW 44 from the company Borchers.

In further embodiments, the thickening agent may be chosen from nonionic homopolymers or copolymers containing ethylenically unsaturated monomers of the amide type, for example, the polyacrylamide products sold under the tradenames Cyanamer® P250 by the company CYTEC.

In further embodiments, the thickening agent chosen from polymers of natural origin may include thickening polymers comprising at least one sugar unit, for instance nonionic guar gums, optionally modified with C1-C6 hydroxyalkyl groups; biopolysaccharide gums of microbial origin, such as scleroglucan gum (also known as *Sclerotium* gum) or xanthan gum; gums derived from plant exudates, such as gum arabic, ghatti gum, karaya gum, gum tragacanth, carrageenan gum, agar gum, carob gum, *Ceratonia siliqua* gum or *Cyamopsis tetragonoloba* (guar) gum; pectins; alginates; starches; hydroxy(C1-C6)alkylcelluloses; or carboxy(C1-C6)alkylcelluloses.

In certain embodiments, the nonionic, unmodified guar gums may be chosen from Guargel D/15 sold by the company Noveon, Vidogum GH 175 sold by the company Unipectine, Meypro-Guar 50 sold by the company Meyhall, or Jaguar® C sold by the company Rhodia Chimie. In other embodiments, the nonionic modified guar gums may be chosen from Jaguar® HP8, HP60, HP120, DC 293 and HP 105 sold by the companies Meyhall and Rhodia Chimie or Galactasol™ 4H4FD2 sold by the company Ashland.

In other embodiments, the thickening agents may be chosen from scleroglucans, for example, Actigum™ CS from Sanofi Bio Industries; Amigel® sold by the company Alban Muller International; xanthan gums, for instance Keltrol®, Keltrol® T, Keltrol® Tf, Keltrol® Bt, Keltrol® Rd, and Keltrol® Cg sold by the company CP Kelco, Rhodicare® S and Rhodicare® H sold by the company Rhodia Chimie; starch derivatives, for instance Primogel® sold by the company Avebe; hydroxyethylcelluloses such as Cellosize® QP3L, QP4400H, QP30000H, HEC30000A and Polymer PCG10 sold by the company Amerchol, Natrosol™ 250HHR, 250MR, 250M, 250HHXR, 250HHX, 250HR, and 250 HX, sold by the company Hercules, or Tylose® H1000 sold by the company Hoechst; hydroxypropylcelluloses, for instance Klucel™ EF, H, LHF, MF, and G, sold by the company Ashland; carboxymethylcelluloses, for instance Blanose® 7M8/SF, refined 7M, 7LF, 7MF, 9M31F, 12M31XP, 12M31P, 9M31XF, 7H, 7M31, and 7H3SXF, sold by the company Ashland, Aquasorb® A500 sold by the company Hercules, Ambergum® 1221 sold by the company Hercules, Cellogen® HP810A and HP6HS9 sold by the company Montello and Primellose® sold by the company Avebe.

In other embodiments, the modified nonionic guar gums may, for example, be modified with C1-C6 hydroxyalkyl groups. Such hydroxyalkyl groups may be chosen from hydroxymethyl, hydroxyethyl, hydroxypropyl, and hydroxybutyl groups.

In certain embodiments, guar gums may be prepared by reacting the corresponding alkylene oxides, such as for example propylene oxides, with guar gum so as to obtain a guar gum modified with hydroxypropyl groups. The hydroxyalkylation ratio, which corresponds to the number of alkylene oxide molecules consumed to the number of free hydroxyl functional groups present on the guar gum, may in certain embodiments range from about 0.4 to about 1.2.

Examples of nonionic guar gums, optionally modified with hydroxyalkyl groups, include those sold under the tradenames Jaguar® HP8, Jaguar® HP60, Jaguar® HP120, Jaguar® DC 293, and Jaguar® HP 105 by the company Rhodia Chimie, and under the tradename Galactasol™ 4H4FD2 by the company Ashland.

In other embodiments, the guar gum may be chosen from those modified with a quaternary ammonium group, such as guar hydroxypropyltrimonium chloride, also sold under the tradename Jaguar® C-13S by the company Rhodia Chimie.

In other embodiments, the celluloses may be chosen from hydroxyethylcelluloses and hydroxypropylcelluloses, such as those sold under the tradenames Klucel™ EF, Klucel™ H, Klucel™ LHF, Klucel™ MF, Klucel™ G, by the company Ashland and under the tradename Cellosize™ PCG-10 by the company Amerchol.

In other embodiments, non-limiting thickening polysaccharides may be chosen from glucans; modified or unmodified starches such as those derived, for example, from cereals such as wheat, corn or rice, vegetables such as golden pea, or tubers such as potato or cassava; amylose, amylopectin, glycogen, dextrans, celluloses or derivatives thereof (methylcelluloses, hydroxyalkylcelluloses, ethylhydroxyethylcelluloses), mannans, xylans, lignins, arabans, galactans, galacturonans, chitin, chitosans, glucoronoxylans, arabinoxylans, xyloglucans, glucomannans, pectic acids or pectins, arabinogalactans, carrageenans, agars, gums arabic, gums tragacanth, Ghatti gums, Karaya gums, carob gums, galactomannans such as guar gums and their nonionic derivatives such as hydroxypropylguar, or mixtures thereof.

In other embodiments, the thickening agent may be chosen from silicas or hydrophobic silicas, such as those described in EP-A-898960, incorporated by reference herein. Examples of such silicas include those sold under the tradename Aerosil® R812 by the company Degussa, CAB-O-SIL® TS-530, CAB-O-SIL® TS-610, CAB-O-SIL® TS-720 by the company Cabot, or Aerosil® R972 and Aerosil® R974 by the company Degussa; clays, such as montmorillonite; modified clays such as the bentones, for example, stearalkonium hectorite, stearalkonium bentonite; or polysaccharide alkyl ethers, optionally with the alkyl group having from 1 to 24 carbon atoms, for example from 1 to 10 carbon atoms, from 1 to 6 carbon atoms, or from 1 to 3 carbon atoms, such as those described in document EP-A-898958, incorporated by reference herein.

In certain embodiments, when an anionic thickening agent is used, it is generally neutralized before being included in, or as it is added to the compositions of the disclosure. Such an anionic thickening agent may be neutralized by employing traditional neutralizing agents such as alkanolamines, for example, monoethanolamine and diethanolamine; aminomethyl propanol; basic amino acids, for example arginine and lysine; or ammonium compounds and their salts. The anionic thickening agent may also be neutralized by a latex polyurethane polymer having at least one free amino group.

In one embodiment of the present invention, the at least one thickening agent is selected from cellulose polymers, gums, modified or unmodified carboxyvinyl polymers, polyacrylamides, copolymers of acrylic acid and of acrylamide, sodium salts of polyhydroxycarboxylic acids, optionally crosslinked and/or neutralized 2-acrylamido-2-methylpropanesulphonic acid polymers and copolymers, polyacrylic acid/alkyl acrylate, glucans, modified or unmodified starches, silicas, and mixtures thereof.

The thickening agent in the compositions of the present invention may be a starch derivative chosen from the compounds of the following formulae:

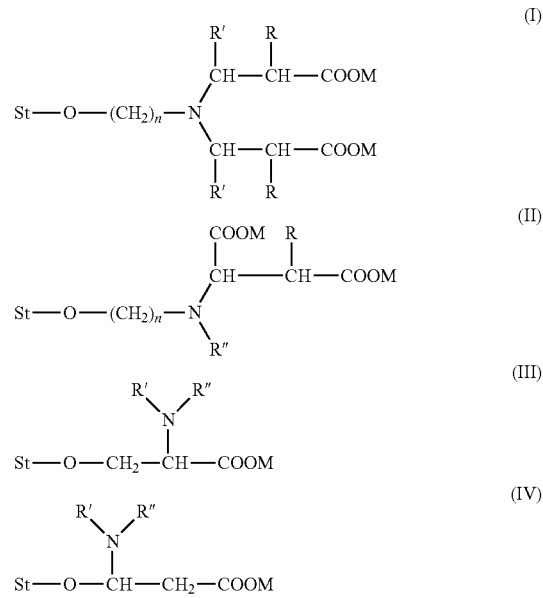

in which formulae:

St-O represents a starch molecule,

R, which may be identical or different, represents a hydrogen atom or a methyl radical, R', which may be identical or different, represents a hydrogen atom, a methyl radical or a —COOH group, n is an integer equal to 2 or 3, M, which may be identical or different, denotes a hydrogen atom, an alkali metal or alkaline-earth metal such as Na, K or Li, $NH_4$, a quaternary ammonium or an organic amine, R" represents a hydrogen atom or an alkyl radical containing from 1 to 18 carbon atoms.

These compounds are disclosed in particular in U.S. Pat. Nos. 5,455,340 and 4,017,460 which are included by way of reference.

The starch molecules may be derived from any plant sources of starch such as, in particular, corn, potato, oat, rice, tapioca, sorghum, barley or wheat. The starch hydrolysates mentioned above may also be used. The starch is preferably derived from potato.

The starches of formula (I) or (II) are used in particular. Starches modified with 2-chloroethylaminodipropionic acid, i.e. the starches of formula (I) or (II) in which R, R' and R" represent a hydrogen atom and n is equal to 2, are used more preferentially.

A preferred starch derivative is known under the INCI name potato starch modified sold under the tradename STRUCTURE® SOLANACE by AkzoNobel.

In one embodiment of the present invention, the at least one thickening agent is selected from hydroxyethylcellulose (also known as HEC), hydroxymethylcellulose, methylhydroxyethylcellulose, hydroxypropylcellulose (also known as HPC), hydroxybutylcellulose, hydroxyethylmethylcellulose (also known as methyl hydroxyethylcellulose) and hydroxypropylmethylcellulose (also known as HPMC), cetyl hydroxyethylcellulose, hydroxypropyl guar gums, acrylate/C10 C30 alkyl acrylate copolymers, carbomers, polyacrylates, potato starch modified, and mixtures thereof.

In one embodiment of the present invention, the at least one thickening agent is chosen from hydroxyethylcellulose, cetyl hydroxyethylcellulose, carbomers, and mixtures thereof.

In one embodiment of the present invention, the at least one thickening agent is present in an amount of from about 0.01% to about 5% by weight, preferably from about 0.05% to about 3% by weight, and most preferably from about 0.1% to about 2% by weight, relative to the total weight of the composition, including all ranges and subranges therebetween.

In one embodiment of the present invention, the at least one thickening agent is present in an amount of from about 0.01% to about 2% by weight, preferably from about 0.05% to about 1% by weight, and most preferably from about 0.1% to about 0.6% by weight, relative to the total weight of the composition, including all ranges and subranges therebetween.

In various embodiments, the thickening agent may be present in an amount of about 0.01%, 0.02%, 0.03%, 0.04%, 0.05%, 0.06%, 0.07%, 0.075%, 0.08%, 0.09%, 0.1%, 0.125%, 0.15%, 0.2%, 0.25% 0.3%, 0.325%, 0.35%, 0.375%, 0.4%, 0.425%, 0.45%, 0.5%, 0.55%, 0.6%, 0.65%, 0.7%, 0.75%, 0.8%, 0.85%, 0.9%, 0.95%, 1%, 1.25%, 1.5%, 1.75%, or 2% by weight, relative to the total weight of the composition.

Nonionic Surfactants

In one embodiment, the compositions of the present invention comprise at least one nonionic surfactant selected from fatty alcohols, alkoxylated fatty alcohols, alkyl(ether) phosphates, alkylpolyglucosides, fatty acid alkanolamides, and mixtures thereof.

Fatty Alcohols

The fatty alcohols correspond to linear, branched saturated/unsaturated fatty alcohols comprising from 6 to 60 carbon atoms and preferably correspond to the formula R—OH in which R is a saturated or unsaturated, linear or branched hydrocarbon-based radical, comprising 6 to 60 carbon atoms, or from 10 to 50 carbon atoms, or from 12 to 24 carbon atoms, or from 10 to 22 carbon atoms optionally comprising one or more OH groups.

The saturated fatty alcohols are preferably branched and can be in liquid form. They can optionally comprise, in their structure, at least one aromatic or non-aromatic ring. They are preferably acyclic.

The unsaturated fatty alcohols exhibit, in their structure, at least one double or triple bond and preferably one or more double bonds. When several double bonds are present, there are preferably 2 or 3 of them and they can be conjugated or unconjugated. These unsaturated fatty alcohols can be linear or branched. They can optionally comprise, in their structure, at least one aromatic or non-aromatic ring. They are preferably acyclic.

Liquid fatty alcohols may be selected, for example, from octyldodecanol, 2-butyloctanol, 2-hexyldecanol, 2-undecylpentadecanol, oleyl alcohol, linoleyl alcohol, isostearyl alcohol, undecylenyl alcohol, linolenyl alcohol and mixtures thereof.

The fatty alcohols of the invention may be in solid form and may be non-oxyalkylenated and/or non-glycerolated. These fatty alcohols may be constituents of animal or plant waxes.

The solid fatty alcohol may represent a mixture of fatty alcohols, which means that several species of fatty alcohol may coexist, in the form of a mixture, in a commercial product. One example of such a commercial product is cetearyl alcohol, a mixture of cetyl alcohol and stearyl alcohol, commercially available under the trade name of LANETTE-O from the company BASF. Cetyl alcohol may also be commercially available under the tradename of LANETTE 16 from the company BASF.

In an embodiment, the solid fatty alcohols of the present invention may be chosen from myristyl alcohol, cetyl alcohol, stearyl alcohol, cetearyl alcohol, and mixtures thereof, octyldodecanol, 2-butyloctanol, 2-hexyldecanol, 2-undecylpentadecanol, oleic alcohol, linoleic alcohol, behenyl alcohol, and mixtures thereof.

Other suitable examples of the solid fatty alcohol of the present invention include branched solid fatty alcohols chosen from 2-dodecylhexadecanol, 2-tetradecyl-1-octadecanol, 2-tetradecyl-1-eicosanol, 2-hexadecyl-1-octadecanol and 2-hexadecyl-1-eicosanol, and mixtures thereof.

In embodiment of the present invention, the fatty alcohol comprises cetyl alcohol and stearyl alcohol or cetearyl alcohol.

In embodiment of the present invention, the fatty alcohol is chosen from cetyl alcohol, stearyl alcohol, cetearyl alcohol, and mixtures thereof.

Alkoxylated Fatty Alcohols

"Alkoxylated fatty alcohol" as used herein means a compound having at least one fatty portion (8 carbon atoms or more) and at least one alkoxylated portion (—(CH$_2$)$_n$O—, where n is an integer from 1 to 5, preferably 2 to 3). According to particularly preferred embodiments, the alkoxylated fatty alcohols of the present invention can be used as non-ionic surfactants, if desired. In this regard, the alkoxylated fatty alcohols of the present invention preferably have an HLB (hydrophilic-lipophilic balance) value from 1-20, including all ranges and subranges therebetween, with HLB values ranging from 1 to 5 (particularly 3 to 5) or from 15-20 (particularly 16 to 18) being most preferred. Preferably, the alkoxylated fatty alcohol is chosen from ethoxylated fatty alcohols, propoxylated fatty alcohols, and mixtures thereof.

Preferably, the alkoxylated fatty alcohol can be chosen from di-alkyl, tri-alkyl- and combinations of di-alkyl and tri-alkyl substituted ethoxylated polymers. They can also be chosen from mono-alkyl, di-alkyl, tri-alkyl, tetra-alkyl substituted alkyl ethoxylated polymers and all combinations thereof. The alkyl group can be saturated or unsaturated, branched or linear and contain a number of carbon atoms preferably from about 12 carbon atoms to about 50 carbon atoms, including all ranges and subranges therebetween, for example, 20 to 40 carbon atoms, 22 to 24 carbon atoms, 30 to 50 carbon atoms, and 40 to 60 carbon atoms. Most preferably, the fatty portion contains a mixture of compounds of varying carbon atoms such as, for example, C20-C40 compounds, C22-C24 compounds, C30-050 compounds, and C40-C60 compounds.

Preferably, the alkoxylated portion of the alkoxylated fatty alcohols of the present invention contain 2 or more alkoxylation units, preferably from 10 to 200 alkoxylation units, preferably from 20 to 150 alkoxylation units, and preferably from 25 to 100 alkoxylation units, including all ranges and subranges therebetween. Also preferably, the alkoxylation units contain 2 carbon atoms (ethoxylation units) and/or 3 carbon atoms (propoxylation units).

The amount of alkoxylation can also be determined by the percent by weight of the alkoxylated portion with respect to the total weight of the compound. Suitable weight percentages of the alkoxylated portion with respect to the total weight of the compound include, but are not limited to, 10 percent to 95 percent, preferably 20 percent to 90 percent, including all ranges and subranges therebetween with 75 percent to 90 percent (particularly 80 percent to 90 percent) or 20 percent to 50 percent being preferred.

Preferably, the alkoxylated fatty alcohols of the present invention have a number average molecular weight (Mn) greater than 500, preferably from 500 to 5,000, including all ranges and subranges therebetween such as, for example, Mn of 500 to 1250 or an Mn of 2,000 to 5,000.

Suitable examples of alkoxylated fatty alcohols include: laureth-3, laureth-7, laureth-9, laureth-12, laureth~23, ceteth-10, steareth-10, steareth-2, steareth-100, beheneth-5, beheneth-5, beheneth-10, oleth-10, Pareth alcohols, trideceth-10, trideceth-12, C12-13 pareth-3, C12-13 pareth-23, C11-15 pareth-7, PPG-5 ceteth-20, PEG-55 Propylene Glycol Oleate, glycereth-26 (PEG-26 Glyceryl Ether), PEG 120 methyl glucose dioleate, PEG 120 methyl glucose trioleate, PEG 150 pentaerythrityl tetrastearate, and mixtures thereof.

Alkyl(ether)phosphates

Suitable alkyl(ether)phosphates include, but are not limited to, alkoxylated alkyl phosphate esters and alkyl phosphate esters corresponding to a mono-ester of formula (I) and salts thereof:

$$RO[CH_2O]_u[(CH_2)_xCH(R')(CH_2)_y(CH_2)_zO]_v[CH_2CH_2O]_w-PO-(OH)_2 \quad \text{Formula (I)};$$

a di-ester corresponding to formula (II) and salts thereof:

$$\{RO[CH_2O]_u[(CH_2)_xCH(R')(CH_2)_y(CH_2)_zO]_v[CH_2CH_2O]_w\}_2PO-(OH) \quad \text{Formula (II)};$$

a tri-ester corresponding to formula (III):

$$\{RO[CH_2O]_u[(CH_2)_xCH(R')(CH_2)_y(CH_2)_zO]_v[CH_2CH_2O]_w\}_3PO \quad \text{Formula (III)}$$

and combinations thereof, wherein:

R is a hydrocarbon radical containing from 6 to 40 carbon atoms;

u, v and w, independently of one another, represent numbers of from 0 to 60;

x, y and z, independently of one another, represent numbers of from 0 to 13;

R' represents hydrogen, alkyl, the sum of x+y+z being ?0. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formulas (I), (II) and (III), R is linear or branched, acyclic or cyclic, saturated or unsaturated, aliphatic or aromatic, substituted or unsubstituted, preferably a linear or branched, acyclic $C_{6-40}$ alkyl or alkenyl group or a $C_{1-40}$ alkyl phenyl group, more particularly a $C_{8-22}$ alkyl or alkenyl group or a $C_{4-18}$ alkyl phenyl group, more preferably a $C_{12-18}$ alkyl group or alkenyl group or a $C_{6-16}$ alkyl phenyl group; u, v, w, independently of one another, is preferably a number from 2 to 20, more preferably a number from 3 to 17 and most preferably a number from 5 to 15;

x, y, z, independently of one another, is preferably a number from 2 to 13, more preferably a number from 1 to 10 and most preferably a number from 0 to 8.

In general, the lower the number of carbon atoms in the R group of the phosphate esters, the more irritating to the skin and the less soluble in water the phosphate ester becomes. In contrast, the higher the number of carbon atoms in the R group, the milder to the skin and the thicker and more waxy the resultant product becomes. Accordingly, for best results, R should have from 12 to 18 carbon atoms.

Particularly preferred alkoxylated alkyl phosphate esters for use in the present invention are PPG-5-Ceteth-10 phosphate (CRODAFOS SG®), Oleth-3 phosphate (CRODAFOS N3 acid), Oleth-10 phosphate (CRODAFOS N10 acid), and a mixture of Ceteth-10 phosphate and Dicetyl phosphate (CRODAFOS CES) all sold by Croda. Particularly preferred alkyl phosphate esters are Cetyl phosphate (Hostaphat CC 100), Stearyl phosphate (Hostaphat CS 120) from Clariant.

In one embodiment, the alkyl(ether)phosphates are chosen from PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate, and mixtures thereof.

Alkylpolyglucosides

The alkyl(poly)glucoside (alkylpolyglycoside) is represented especially by the following general formula:

$$R_1O-(R_2O)_t-(G)_v$$

wherein:

$R_1$ represents a linear or branched alkyl or alkenyl radical comprising 6 to 24 carbon atoms and especially 8 to 18 carbon atoms, or an alkylphenyl radical whose linear or branched alkyl radical comprises 6 to 24 carbon atoms and especially 8 to 18 carbon atoms;

$R_2$ represents an alkylene radical comprising 2 to 4 carbon atoms,

G represents a sugar unit comprising 5 to 6 carbon atoms, t denotes a value ranging from 0 to 10 and preferably 0 to 4, v denotes a value ranging from 1 to 15 and preferably 1 to 4.

Preferably, the alkylpolyglycoside surfactants are compounds of the formula described above in which:

$R_1$ denotes a linear or branched, saturated or unsaturated alkyl radical comprising from 8 to 18 carbon atoms, $R_2$ represents an alkylene radical comprising 2 to 4 carbon atoms, t denotes a value ranging from 0 to 3 and preferably equal to 0, G denotes glucose, fructose or galactose, preferably glucose;

the degree of polymerization, i.e. the value of v, possibly ranging from 1 to 15 and preferably from 1 to 4; the mean degree of polymerization more particularly being between 1 and 2.

The glucoside bonds between the sugar units are generally of 1-6 or 1-4 type and preferably of 1-4 type. Preferably, the alkyl(poly)glycoside surfactant is an alkyl(poly)glucoside surfactant. C8/C16 alkyl(poly)glycosides 1,4, and especially decyl glucosides and caprylyl/capryl glucosides, are most particularly preferred.

Among the commercial products, mention may be made of the products sold by the company COGNIS under the names PLANTAREN® (600 CS/U, 1200 and 2000) or PLANTACARE® (818, 1200 and 2000); the products sold by the company SEPPIC under the names ORAMIX CG 110 and ORAMIX NS 10; the products sold by the company BASF under the name LUTENSOL GD 70, or else the products sold by the company CHEM Y under the name AG10 LK.

Preferably, use is made of C8/C16-alkyl(poly)glucosides 1,4, especially as an aqueous 53% solution, such as those sold by Cognis under the reference Plantacare® 818 UP.

In an embodiment, the alkylpolyglucoside is chosen from decyl glucoside, stearyl glucoside, lauryl glucoside, coco-glucoside, cetearyl glucoside, decyl lauryl glucoside, and mixtures thereof.

Fatty Acid Alkanolamides

Suitable fatty acid alkanolamides include those formed by reacting an alkanolamine and a C6-C36 fatty acid. Such surfactants can be chosen from mono-alkanolamides and di-alkanolamides of C6-C36 fatty acids, and preferably from mono-alkanolamides and di-alkanolamides of C8-C30 fatty acids or of C8-C24 fatty acids, and may have a C2-3 hydroxyalkyl group. Examples thereof include, but are not limited to:

oleic acid diethanolamide, oleic acid monoisopropanol-amide, myristic acid monoethanolamide, soya fatty acids diethanolamide, stearic acid ethanolamide, linoleic acid diethanolamide, behenic acid monoethanolamide, isostearic acid monoisopropanolamide, erucic acid diethanolamide, ricinoleic acid monoethanolamide, coconut isopropanol-amide (INCI name: Cocamide MIPA), coconut fatty acid monoethanolamide (INCI name: Cocamide MEA), coconut fatty acid diethanolamide, palm kernel fatty acid diethanolamide, lauric monoethanolamide, lauric diethanolamide, lauric isopropanolamide polyoxyethylene coconut fatty acid monoethanolamide, and mixtures thereof.

In an embodiment, the fatty acid alkanolaminde is chosen from Cocamide MIPA, Cocamide MEA (Coco monoethanolamide), and mixtures thereof.

In one embodiment of the present invention, the at least one nonionic surfactant is selected from cetyl alcohol, stearyl alcohol, cetearyl alcohol (mixture of cetyl alcohol and stearyl alcohol), octyldodecanol, isostearyl alcohol, 2-hexyl decanol, palmityl alcohol, myristyl alcohol, stearyl alcohol, lauryl alcohol, oleic alcohol (or oleyl), linoleyl alcohol (or linoley-ether), linolenic alcohol (or linolenyl) and undecylenic alcohol, and mixtures thereof, and more preferably from cetyl alcohol, stearyl alcohol, and cetearyl alcohol, PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate, laureth-7, laureth-9, trideceth-10, trideceth-12, C12-13 pareth-3, C12-13 pareth-23, C11-15 pareth-7, PPG-5 ceteth-20, PEG-55 Propylene Glycol Oleate, glycereth-26, decyl glucoside, cetearyl glucoside, decyl lauryl glucoside, stearyl glucoside, coco-glucoside, cocamide MIPA, and mixtures thereof.

The at least one nonionic surfactant is present in the compositions of the present invention in an amount of from about 0.01% to about 10% by weight, preferably from about 0.05% to about 9% by weight, or more preferably from about 0.08% to about 8% by weight, relative to the total weight of the composition, including all ranges and sub ranges therebetween.

In a particular embodiment, the total amount of anionic surfactants is at about 1%, 1.25%, 1.5%, 1.55%, 1.6%, 1.65%, 1.7%, 1.75%, 1.8%, 1.85%, 1.9%, 1.95%, 2%, 2.05%, 2.1%, 2.15%, 2.2%, 2.25%, 2.3%, 2.35%, 2.4%, 2.45%, 2.5%, 2.55%, 2.6%, 2.65%, 2.7%, 2.75%, 2.8%, 2.85%, 2.9%, 3.0%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5 8.75%, 9%, 9.25%, 9.5%, 9.75%, or 10%, by weight, relative to the total weight of the composition.

Cationic Conditioning Polymer

The composition according to the invention may further comprise at least one cationic polymer. The cationic conditioning polymer that can be used in the invention comprises homopolymers, copolymers, and mixtures thereof.

In one embodiment, the at least one cationic conditioning polymer is selected from cationic cellulose derivatives, cationic gum derivatives, polymer derivatives of diallyldimethyl ammonium chloride, polymer derivatives of methacrylamidopropyltrimethylammonium chloride, and mixtures thereof.

Non-limiting examples of cationic conditioning polymers useful in the invention include, for example, cationic cellulose derivatives, such as for example polyquaternium-10; cationic gum derivatives such as for example gum derivatives, including particularly guar hydroxypropyltrimonium chloride; polymer derivatives of diallyldimethyl ammonium chloride ("poly-DADMAs") and of methacrylamidopropyltrimethylammonium chloride ("poly-MAPTACs"), and mixtures thereof.

Non-limiting examples of poly-DADMAs and poly-poly-MAPTACs include, polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, and mixtures thereof.

In one embodiment, the at least one cationic conditioning polymer of the present invention is chosen from guar hydroxypropyltrimonium chloride. Such products are marketed under the trade designations including Jaguar® C13 S, Jaguar® C 15, JAGUAR® C 17 by Rhodia.

In one embodiment, the at least one cationic conditioning polymer of the present invention is chosen from polyquaternium-7, polyquaternium-10, guar hydroxypropyltrimonium chloride, and mixtures thereof.

The cationic conditioning polymer is in an amount ranging from about 0.01% to about 4% by weight, preferably from about 0.05% to about 3% by weight, and most preferably from about 0.05% to about 2% by weight, relative to the total weight of the composition, including all ranges and sub ranges therebetween.

The amount of the at least one cationic conditioning polymer can be about 0.1%, 0.13%, 0.15%, 0.17%, 0.18%, 0.19%, 0.2%, 0.21%, 0.22%, 0.23%, 0.24%, 0.25%, 0.28%, 0.3%, 0.33%, 0.35%, 0.38%, 0.4%, 0.43%, 0.46%, 0.48, 0.5%, 0.525%, 0.55%, 0.575%, 0.6%, 0.625%, 0.65%, 0.67%, 0.7%, 0.725%, 0.75%, 0.775%, 0.8%, 0.825%, 0.85%, 0.875%, 0.9%, 0.925%, 0.95%, 0.975%, 1%, 1.25%, 1.5%, 1.75%, 2% by weight, relative to the total weight of the composition.

Neutralizing Agents

The compositions of the present invention may further comprise at least one neutralizing agent wherein the at least one neutralizing agent is selected from organic amines, alkali metal hydroxides, alkali earth metal hydroxides, alkali metal carbonates, alkali metal phosphates, and mixtures thereof, Organic amines may be chosen from organic amines comprising one or two primary, secondary, or tertiary amine functions, and at least one linear or branched C1-C8 alkyl groups bearing at least one hydroxyl radical.

Organic amines may also be selected cyclic amines and other cyclic compounds, saturated or unsaturated, having one or more nitrogen atoms within the ring, and mixtures thereof.

The organic amines may be chosen from the ones having a pKb at 25° C. of less than 12, such as less than 10 or such as less than 6. It should be noted that this is the pKb corresponding to the function of highest basicity.

Organic amines may also be chosen from alkanolamines such as mono-, di- or trialkanolamines, comprising one to three identical or different C1-C4 hydroxyalkyl radicals, ethylamines, ethyleneamines, quinoline, aniline and cyclic amines, such as pyrroline, pyrrole, pyrrolidine, imidazole, imidazolidine, imidazolidinine, morpholine, pyridine, piperidine, pyrimidine, piperazine, triazine and derivatives thereof.

Among the compounds of the alkanolamine type that may be mentioned include but not limited to: monoethanolamine (also known as monoethanolamine or MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, 2-amino-2-methyl-1-propanol (aminomethyl propanol), and tris(hydroxymethylamino)methane.

Other examples include but are not limited to: 1,3-diaminopropane, 1,3-diamino-2-propanol, spermine, and spermidine.

In some embodiments, the organic amines are chosen from amino acids.

As non-limiting examples, the amino acids that may be used may be of natural or synthetic origin, in L, D, or racemic form, and comprise at least one acid function chosen from, for instance, carboxylic acid, sulfonic acid, phosphonic acid, and phosphoric acid functions. The amino acids may be in their neutral or ionic form.

Further as non-limiting examples, the amino acids may be chosen from basic amino acids comprising an additional amine function optionally included in a ring or in a ureido function.

Amino acids that may be used in the present disclosure include but are not limited to: aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine, ornithine, citrulline, and valine.

In some embodiments, the organic amines are chosen from organic amines of heterocyclic type. Besides histidine that has already been mentioned in the amino acids, non-limiting mention may also be made of pyridine, piperidine, imidazole, 1,2,4-triazole, tetrazole, and benzimidazole.

In some embodiments, the organic amines are chosen from amino acid dipeptides. Amino acid dipeptides that may be used in the present disclosure include but not limited to: carnosine, anserine, and baleine.

In some embodiments, the organic amines are chosen from compounds comprising a guanidine function. Organic amines of this type that may be used in the present disclosure include, besides arginine that has already been mentioned as an amino acid, creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

The alkali metal phosphates and carbonates that may be used are, for example, sodium phosphate, potassium phosphate, sodium carbonate, sodium bicarbonate, potassium carbonate, potassium bicarbonate, and their derivatives.

Neutralizing agents may also be chosen from alkali metal hydroxides, alkaline-earth metal hydroxides, transition metal hydroxides, quaternary ammonium hydroxides, organic hydroxides, and mixtures thereof. Suitable examples are ammonium hydroxide, sodium hydroxide, potassium hydroxide, lithium hydroxide, rubidium hydroxide, caesium hydroxide, francium hydroxide, beryllium hydroxide, magnesium hydroxide, calcium hydroxide, strontium hydroxide, barium hydroxide, molybdenum hydroxide, manganese hydroxide, zinc hydroxide, cobalt hydroxide, cadmium hydroxide, cerium hydroxide, lanthanum hydroxide, actinium hydroxide, thorium hydroxide, aluminium hydroxide, guanidinium hydroxide and mixtures thereof.

According to at least one embodiment, the at least one neutralizing agent is chosen from aminomethyl propanol, sodium hydroxide, potassium hydroxide, lithium hydroxide, aminomethyl propanediol, triisopropanol amine, dimethylstearylamine, dimethyl/tallowamine, lysine, ornithine, arginine, monoethanolamine, triethanolamine, calcium hydroxide, calcium bicarbonate, and mixtures thereof.

According to another preferred embodiment, the at least one neutralizing agent is chosen from aminomethyl propanol, sodium hydroxide, lithium hydroxide, calcium hydroxide, monoethanolamine, and mixtures thereof.

The at least neutralizing agent may be present in an amount of from 0.01% to 3% by weight, preferably from 0.02% to 2.75% by weight, more preferably from 0.025% to 2.5% by weight, even more preferably from 0.03% to 2% by weight, relative to the total weight of the composition, including all ranges and sub ranges therebetween.

When the at least neutralizing agent is selected from aminomethyl propanol, it is present in an amount of from 0.1% to 6.3% by weight, preferably from 0.2% to 5.5% by weight, more preferably from 0.3% to 5% by weight, even more preferably from 0.3% to 4.6% by weight, relative to the total weight of the composition, including all ranges and sub ranges therebetween.

When the at least neutralizing agent is selected from sodium hydroxide, it is present in an amount of from 0.1% to 4.1% by weight, preferably from 0.15% to 3.5% by weight, more preferably from 0.2% to 3% by weight, even more preferably from 1% to 3% by weight, relative to the total weight of the composition, including all ranges and sub ranges therebetween.

When the at least neutralizing agent is selected from monoethanolamine, it is present in an amount of from 0.1% to 4.1% by weight, preferably from 0.15% to 3.5% by weight, more preferably from 0.2% to 3% by weight, even more preferably from 1% to 3% by weight, relative to the total weight of the composition, including all ranges and sub ranges therebetween.

pH

The pH of the compositions of the present invention may range from about 2 to less than 7, or from about pH 2.5 to about 6.5, or from about pH 3 to about 6, or from about pH 3 to about 5.2, such as from about pH 3 to about 5, or preferably from about pH 3 to about 4.8, or more preferably from about pH 3 to about 4.5, or even more preferably from about pH 3 to about 4, including all ranges and sub ranges therebetween.

In some embodiments, the pH of the compositions of the present invention can be at about 2, 2.5, 2.75, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5.

The desired pH may be obtained by using one or more of the neutralizing agents described above.

Water

The compositions according to the invention comprise water. The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from EauxBonnes, water from Rochefort, water from Saint Christau, water from Les Fumades, water from Tercis-les-Bains or water from Avene. Water may also comprise reconstituted thermal water, that is to say a water comprising trace elements such as zinc, copper, magnesium, etc., reconstituting the characteristics of a thermal water.

The composition according to the invention may comprise water in an amount ranging from about 50% to about 99% by weight, preferably from about 65% to about 95% by weight, and most preferably from about 70% to about 92% by weight, relative to the total weight of the composition.

Organic Solvent (Optional)

The compositions according to the invention optionally may comprise one or more organic solvent.

Non-limiting examples of organic solvents useful in the invention include, for example, glycols and polyols containing from 2 to 8 carbon atoms, such as ethylene glycol, propylene glycol, 1,3-butylene glycol, pentylene glycol, hexylene glycol, dipropylene glycol, glycerin, and mixtures thereof.

Other non-limiting examples of organic solvents useful in the invention include, for example, lower carbon alcohols such as ethanol, propanol, isopropanol, and mixtures thereof.

When present in the composition according to the invention, the water-soluble solvent is preferably present in the composition according to the invention in an amount of from about 0.01% to 10% by weight, preferably in an amount of from about 0.05% to 5% by weight, and most preferably 0.1% to 1% by weight, based on the total weight of the composition.

The composition according to the invention may also comprise at least one additional component selected from organic solvents, silicones, plasticizers, opacifiers, plant/vegetable oils, hydrocarbons, lower alkanes, fragrance, preservatives, pH adjusters, plant extracts, salts, vitamins, sunscreens, colorants, and mixtures thereof.

A person skilled in the art will take care to select the optional additional components and the amount thereof such that they do not harm the properties of the compositions of the present invention.

These additional components are generally present in the composition according to the invention in an amount ranging from about 0 to about 20% by weight relative to the total weight of the composition.

In one embodiment, the hair cosmetic composition of the present invention is an aqueous composition and may be provided in the form of a shampoo or cleanser.

With respect to the anti-yellowing effect, while the images in FIG. 1 are in black and white and do not show the actual yellow or bleached appearance of the bleached hair (without treatment) and hair treated with the comparative and inventive examples, it can be seen that the shade of the hair subjected to protocol I is darker ($4^{th}$ and $6^{th}$ swatches from the left) and the shade of the hair subjected to protocol II is lighter ($3^{rd}$ and $5^{th}$ swatches from the left) and comparable to the shade of the bleached hair without treatment ($2^{nd}$ swatch from left).

Thus, the darker shade for the $4^{th}$ and $6^{th}$ swatches indicate that the use of Protocol I (with heating step) resulted in a better masking of the yellow tint or anti-yellowing effect on the hair treated with either the comparative and inventive formulas as compared to the observed anti-yellowing effect on the hair treated according to Protocol II (without heating step) and on bleached hair. The better anti-yellowing effect was evident from the color of the hair which visually appeared darker. However, while comparable anti-yellowing effects can be observed for both inventive and comparative formula when Protocol I is employed, the attributes of manageability and discipline were observed to be better for the hair treated with the inventive formulas in accordance with Protocols I and II. Thus, overall, the treatment of hair with the inventive formulas according to Protocols I and II resulted in generally better cosmetic visual and sensory attributes imparted to hair and at the same time, the treatment of bleached hair with either comparative or inventive formula according to Protocol I resulted in better anti-yellowing effects on hair.

In one embodiment, the present invention is related to a method or process of cleansing hair, wherein the hair cosmetic composition is applied onto hair (wet or dry), massaged into the hair fibers, then rinsed out with water.

In one embodiment, the present invention is related to a process or method of cleansing hair according to the general protocol or treatment cycle involving the steps of:

a) optionally, washing/rinsing the hair with a shampoo having a neutral pH and/or rinsing the hair with water, followed by allowing the hair to air dry, while optionally applying a smoothing action on the hair;

b) applying the composition onto the hair;

c) allowing the composition to remain on the hair for a period of time ranging from about 1 to about 10 minutes or from about 1 to about 5 minutes;

d) rinsing the hair with water;

e) drying the hair at a temperature ranging from room temperature up to about 100° C., while optionally applying a smoothing action on the hair;

f) passing a flat iron over the hair swatch at least once, or such as two times up to 10 times or such as three times up to 10 times wherein the flat iron is employed at a temperature of about 100° C., or ranging from about 100° C. to about 250° C. or from about 110° C. to about 230° C. or from about 110° C. to about 210° C. or from about 120° C. to about 200° C. or from about 150° C. to about 190° C., or from about 190° C. to about 230° C., including ranges and sub-ranges therebetween, or at a temperature of about 230° C. or about 225° C. or about 220° C. or about 210° C. or about 200° C. or about 190° C. or about 180° C. or about 150° C. or about 100° C. and preferably at about 230° C.; and g) washing/rinsing the hair with a shampoo having a neutral pH and/or rinsing the hair with water, followed by allowing the hair to air dry, while optionally applying a smoothing action on the hair.

The smoothing action may be conducted by brushing or combing or passing the fingers through the hair.

Drying the hair at a temperature ranging from room temperature up to about 100° C. may be accomplished by drying the hair with a blow dryer device or using other heat sources such as a flat iron, a hair dryer, a heat lamp, a heat wand, or other similar devices.

In various embodiments, the flat iron is passed over the hair at least once or from one time up to 10 times or from 2 times up to 10 times or from 3 times up to 10 times or from 5 times up to 10 times or from 6 times up to 10 times or 10 times.

The composition can be applied and spread onto the hair using an applicator device or with the hands or gloved hands or with the fingers. A suitable applicator device is an applicator brush or applicator comb or applicator spatula or a dispenser or applicator tip attached to the container holding the composition.

The method or treatment cycle described above may be repeated over a period of days or weeks.

The process of cleansing with the hair cosmetic composition of the invention may be followed by the a second cosmetic composition, such as a conditioner, which is applied onto the wet hair, left on the hair from 0 up to about 10 minutes, while optionally massaging the second cosmetic composition onto the hair fibers, then rinsed out with water.

The cosmetic effects imparted by the compositions and accompanying methods of treating the hair of the present invention may be evaluated by visually assessing the appearance of the hair after processing the hair according to the methods of the invention. Another type of evaluation can also involve sensorial evaluations of the hair.

It was surprisingly and unexpectedly discovered that the hair contacted with the compositions of the invention and treated according to the methods of the invention visually generally appeared to be more extended and/or straight, less volumized, and less frizzy compared to hair contacted with compositions that did not contain thiolactic acid. It was also surprisingly and unexpectedly discovered that the hair contacted with the compositions of the invention and treated according to the methods of the invention were smoother to the touch, more manageable, more disciplined (i.e., less or no fly-aways), and exhibited more regularity with respect to shape and appearance. These effects were even more observable after subjecting the hair to multiple treatment or application cycles.

The compositions of the present invention may be packaged in any suitable container such as a tube, a jar or a bottle. In certain embodiments, the composition can be packaged in a tube or bottle, for example, a squeeze tube or squeeze bottle. Additionally, an applicator device can be attached or connected to the opening of the packaging/squeeze tube or bottle wherein the applicator device is a brush or a comb with teeth such that the ends of the teeth have openings from which the composition of the invention can flow through and be applied directly onto the hair.

The composition of the present invention may also be provided as component of a kit for treating or cleansing hair wherein the kit can additionally contain other components such as a conditioner.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The compositions according to the invention can be manufactured by known processes used generally in the cosmetics, including the processes described in the examples below.

The following Examples are intended to be non-restrictive and explanatory only, with the scope of the disclosed embodiments.

The ingredient amounts in the compositions/formulas described below are expressed in % by weight, based on the total weight of the composition.

EXAMPLES

Example A—Formulations

Shampoo formulas of the present invention can be prepared in water according to Table 1.

| Ingredient | % by Weight (active matter, "AM") |
| --- | --- |
| Anionic surfactants (eg, sodium laureth sulfate, sodium lauryl sulfate, sodium lauroyl sarcosinate, disodium laureth sulfosuccinate, sodium lauryl sulfoacetate, sodium cocoyl isethionate, or mixtures thereof) | 5-20 |
| Amphoteric surfactants (eg, coco betaine, cocamidopropylbetaine, cocoamphoacetate, cocoamphodiacetate, and their salts, or mixtures thereof) | 0.1-10 |
| Thiolactic acid | 0.5-15 |
| Thickening agents (e.g., carbomer, hydroxyethylcellulose) | 0.01-2 |
| Nonionic surfactants (e.g., fatty alcohols, alkoxylated fatty alcohols, alkyl(ether)phosphates, alkylpolyglucosides, fatty acid alkanolamides, or mixtures thereof) | 0.01-10 |
| Cationic conditioning polymers compounds (e.g., quaternary ammonium compounds such as polyquaternium compounds) | 0.01-4 |

| Ingredient | % by Weight (active matter, "AM") |
|---|---|
| Silicones (eg, amodimethicone, divinyl dimethicone/dimethicone copolymer, dimethicone, or mixtures thereof) | 0-10 |
| Water, organic solvent, and additional components such as fragrance, preservatives, pH adjusting agents, plant extracts, plant oils, hydrolyzed proteins vitamins, salt, and fragrances, opacifiers (e.g., glycol distearate), plasticizers, salts, vitamins, sunscreens, lower alkanes, hydrocarbons, colorants, or mixtures thereof (as needed or desired) | Q.S. 100 |

Examples of the inventive shampoo formulas containing 1, 2.5, 5, and 8% by weight of thiolactic acid, based on the total weight of the composition, and comparative formulas which do not contain thiolactic acid were prepared and are presented in the table below.

TABLE 2

Sulfate-based Shampoo Formulas

| US INCI NAME | Comparative formula | Inventive formulas | | | |
|---|---|---|---|---|---|
| | Example 1 | Example 2 | Example 3 | Example 4 | Example 5 |
| | % by weight | | | | |
| SODIUM LAURETH SULFATE | 17.6 (12.3% AM) | 17.6 (12.3% AM) | 17.6 (12.3% AM) | 17.6 (12.3% AM) | 17.6 (12.3% AM) |
| DISODIUM COCOAMPHODIACETATE | 1.61 (0.51% AM) | 1.61 (0.51% AM) | 1.61 (0.51% AM) | 1.61 (0.51% AM) | 1.61 (0.51% AM) |
| COCO-BETAINE | 4.4 (1.32% AM) | 4.4 (1.32% AM) | 4.4 (1.32% AM) | 4.4 (1.32% AM) | 4.4 (1.32% AM) |
| COCAMIDE MIPA | 0.7 | 0.7 | 0.7 | 0.7 | 0.7 |
| THIOLACTIC ACID | — | 1 | 2.5 | 5 | 8 |
| CARBOMER | 0.15 | 0.15 | 0.15 | 0.15 | 0.15 |
| GUAR HYDROXYPROPYL-TRIMONIUM CHLORIDE | 0.2 | 0.2 | 0.2 | 0.2 | 0.2 |
| GLYCOL DISTEARATE | 1.61 | 1.61 | 1.61 | 1.61 | 1.61 |
| DIMETHICONE | 1.88 | 1.88 | 1.88 | 1.88 | 1.88 |
| THEOBROMA CACAO (COCOA) SEED BUTTER | 0.01 | 0.01 | 0.01 | 0.01 | 0.01 |
| Additional Components (e.g., fragrance, preservatives, pH adjusting agents, organic solvent, plant extracts, plant oils, hydrolyzed proteins vitamins, salt, and fragrances, opacifiers (e.g., glycol distearate), plasticizers, salts, vitamins, sunscreens, lower alkanes, hydrocarbons, colorants, or mixtures thereof) | 2.2 | 2.2 | 2.2 | 2.2 | 2.2 |
| Water | QS 100 | QS 100 | QS 100 | QS 100 | QS 100 |
| pH | 5.3 | 3.5 | 3.5 | 3.5 | 3.5 |

TABLE 3

Sulfate-free Shampoo Formulas

| US INCI NAME | Comparative formula | Inventive formulas | | | |
|---|---|---|---|---|---|
| | Example 6 | Example 7 | Example 8 | Example 9 | Example 10 |
| | % by weight | | | | |
| SODIUM LAUROYL SARCOSINATE | 7.2 (2.16% AM) | 7.2 (2.16% AM) | 7.2 (2.16% AM) | 7.2 (2.16% AM) | 7.2 (2.16% AM) |

TABLE 3-continued

Sulfate-free Shampoo Formulas

| US INCI NAME | Comparative formula Example 6 | Inventive formulas | | | |
|---|---|---|---|---|---|
| | | Example 7 | Example 8 | Example 9 | Example 10 |
| DISODIUM LAURETH SULFOSUCCINATE (and) SODIUM LAURYL SULFOACETATE | 40.5 (10.1% AM) | 40.5 (10.1% AM) | 40.5 (10.1% AM) | 40.5 (10.1% AM) | 40.5 (10.1% AM) |
| SODIUM COCOYL ISETHIONATE | 9 (7.3% AM) | 9 (7.3% AM) | 9 (7.3% AM) | 9 (7.3% AM) | 9 (7.3% AM) |
| COCAMIDOPROPYL BETAINE | 4.74 (1.8% AM) | 4.74 (1.8% AM) | 4.74 (1.8% AM) | 4.74 (1.8% AM) | 4.74 (1.8% AM) |
| THIOLACTIC ACID | — | 1 | 2.5 | 5 | 8 |
| CARBOMER | 0.2 | 0.2 | 0.2 | 0.2 | 0.2 |
| DECYL GLUCOSIDE | 0.93 | 0.93 | 0.93 | 0.93 | 0.93 |
| PROPYLENE GLYCOL (and) PEG-55 PROPYLENE GLYCOL OLEATE (ester) | 0.7 (0.28% AM ester) | 0.7 (0.28% AM ester) | 0.7 (0.28% AM ester) | 0.7 (0.28% AM ester) | 0.7 (0.28% AM ester) |
| PPG-5-CETETH-20 | 0.5 | 0.5 | 0.5 | 0.5 | 0.5 |
| GLYCOL DISTEARATE | 1.8 | 1.8 | 1.8 | 1.8 | 1.8 |
| POLYQUATERNIUM-10 | 0.3 (0.273% AM) | 0.3 (0.273% AM) | 0.3 (0.273% AM) | 0.3 (0.273% AM) | 0.3 (0.273% AM) |
| POLYQUATERNIUM-7 | 4.44 (0.4% AM) | 4.44 (0.4% AM) | 4.44 (0.4% AM) | 4.44 (0.4% AM) | 4.44 (0.4% AM) |
| DIVINYLDIMETHICONE/DIMETHICONE COPOLYMER | 0.45 | 0.45 | 0.45 | 0.45 | 0.45 |
| AMODIMETHICONE | 0.4 | 0.4 | 0.4 | 0.4 | 0.4 |
| C12-13 PARETH-3 | 0.016 | 0.016 | 0.016 | 0.016 | 0.016 |
| C12-13 PARETH-23 | 0.016 | 0.016 | 0.016 | 0.016 | 0.016 |
| C11-15 PARETH-7 | 0.16 | 0.16 | 0.16 | 0.16 | 0.16 |
| LAURETH-9 | 0.08 | 0.08 | 0.08 | 0.08 | 0.08 |
| TRIDECETH-12 | 0.04 | 0.04 | 0.04 | 0.04 | 0.04 |
| Additional Components (e.g., fragrance, preservatives, pH adjusting agents, organic solvent, plant extracts, plant oils, hydrolyzed proteins vitamins, salt, and fragrances, opacifiers (e.g., glycol distearate), plasticizers, salts, vitamins, sunscreens, lower alkanes, hydrocarbons, colorants, or mixtures thereof) | 2.11 | 2.11 | 2.11 | 2.11 | 2.11 |
| Water | QS 100 | QS 100 | QS 100 | QS 100 | QS 100 |
| pH | 6.3 | 3.5 | 3.5 | 3.5 | 3.5 |

In making the Formulas in Table 2, the following procedure was used:

The anionic surfactants were combined with a thickening or viscosity modifying agent such as carbomer in an aqueous solution. The dimethicone was stirred into the solution for a few minutes. As a separate mixture, guar hydroxypropyltrimonium chloride and the cocamide mipa were added to water (in an amount of about 20% by weight of the total amount of water in the formula) with fast stirring and heating up to 70° C. After solubilization of these raw materials, the separate mixture was cooled and added to the rest of the formula, and the resulting mixture was stirred for about 15 minutes. A thickening or viscosity modifying agent, such as glycol distearate, was added and mixed. Coco betaine and finally the fragrance and thiolactic acid were added. If necessary, pH was adjusted with Citric Acid or Sodium Hydroxide. Also, if necessary, viscosity was adjusted with hexylene glycol or sodium chloride.

In making the Formulas in Table 3, the following procedure was used:

The polyquaternium-10 was added into water and the resulting solution mixed for complete hydration. The surfactants sodium cocoyl isethionate, disodium laureth sulfosuccinate (and) sodium lauryl sulfoacetate and propylene glycol (and) peg-55 propylene glycol oleate were added in the solution, and the solution was mixed until completely dispersed. The carbomer was added and the temperature was raised to 50° c. As a separate mixture, glycol distearate and cocamidopropyl betaine were added to water (in an amount of about 5% by weight of the total amount of water in the formula) with fast stirring and heating up to 70° C. The separate mixture was added to the rest of the formula, and the resulting mixture was stirred for about 15 minutes, while cooling. When the temperature was close to 30° C., the other raw materials were added, including the thiolactic acid. If necessary, pH was adjusted with Citric Acid or Sodium Hydroxide. Also, if necessary, viscosity was adjusted with PPG-5-ceteth-20 or propylene glycol (and) PEG-55 propylene glycol oleate.

Optional ingredients and additives were included in the formulas: for example, organic solvents, fragrance, preservatives, plant oils and extracts, neutralizing agents, cationic conditioning polymers, silicones, opacifiers, plasticizers, salts, vitamins, sunscreens, lower alkanes, hydrocarbons, colorants, or mixtures thereof.

Example B: Performance Evaluation

Application Protocol

The formulas above were used to treat hair swatches according to the following hair treatment protocol:

1. The hair swatches were washed with a shampoo having a neutral pH, rinsed with water, and the hair was dried at a temperature ranging from room temperature up to about 100° C. by using for example, a blow dryer, while optionally applying a smoothing action on the hair (this step may be an optional step).

2. Each formula was spread along the length of the hair swatches and allowed to remain on the hair for about 5 minutes.

3. The hair swatches were rinsed with water and the hair was dried at a temperature ranging from room temperature up to about 100° C. by using for example, a blow dryer, while optionally applying a smoothing action on the hair.

4. A flat iron was passed over each hair swatch 3 times at about 230° C.

5. The hair swatches were washed with a shampoo having a neutral pH, rinsed with water, and allowed to air dry.

6. The hair swatches were subjected to sensorial and visual assessments with respect to the attributes of straightening, volume and frizz based on a standardized rating scale of 1 to 4, with 4 being the best rating (highest degree of straightening, least amount of volume and least amount of frizziness).

In order to evaluate the long-lasting performance of the formulas on hair over time, the hair swatches were also subjected to multiple applications (from 2 to 5 applications) according to the protocol above based on the common practice of people of washing/cleansing their hair 2 to 3 times a week. One application corresponds to one treatment cycle comprising steps 1 to 5. Five applications or five treatment cycles were designed to simulate washing/cleansing of hair over a two week period (people tend to wash their hair 2 to 3 times a week).

Figure 2:
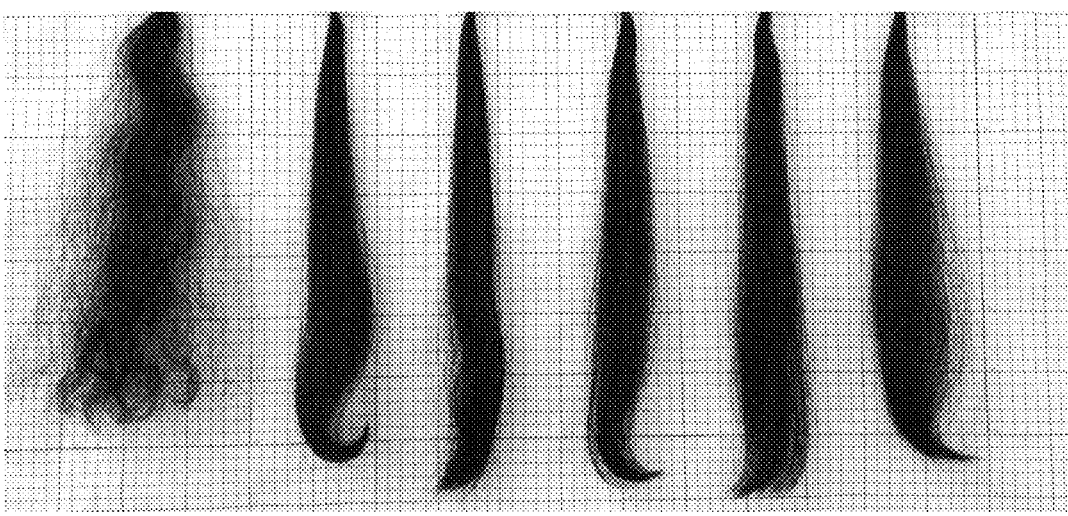
FIG. 2 provides images of hair swatches treated according to two application or treatment cycles including applying inventive or comparative sulfate-based shampoo formulas onto hair and heating the hair at a temperature of equal to or greater than 50° C.
Figure 3:
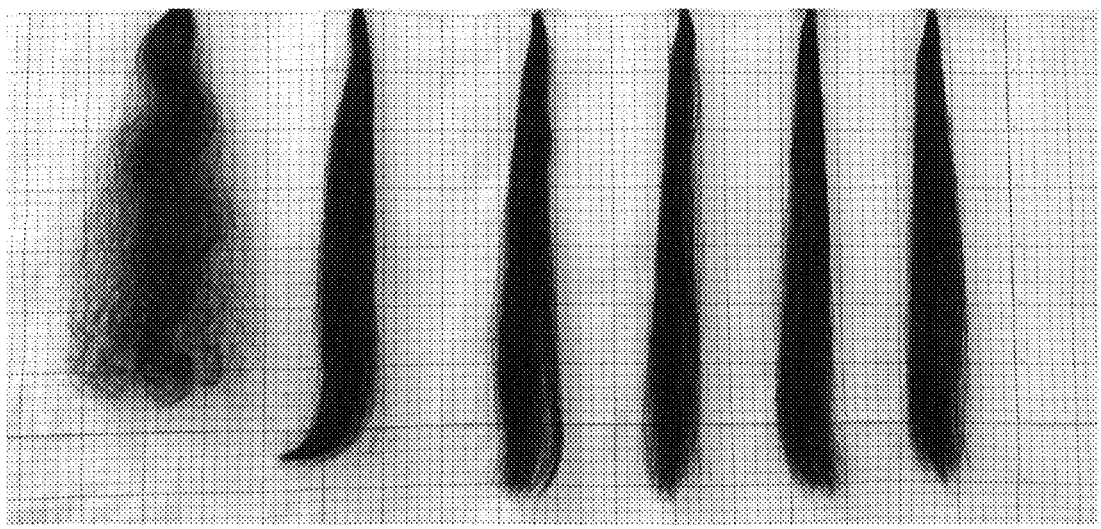
FIG. 3 provides images of hair swatches treated according to five application or treatment cycles including applying inventive or comparative sulfate-based shampoo formulas onto hair and heating the hair at a temperature of equal to or greater than 50° C.

FIGS. 1 to 3 are photographic images of the hair swatches treated with the inventive and comparative sulfate-based shampoo formulas and subjected to several applications or treatment cycles (at $1^{st}$, $2^{nd}$, and $5^{th}$ applications).

Figure 4:
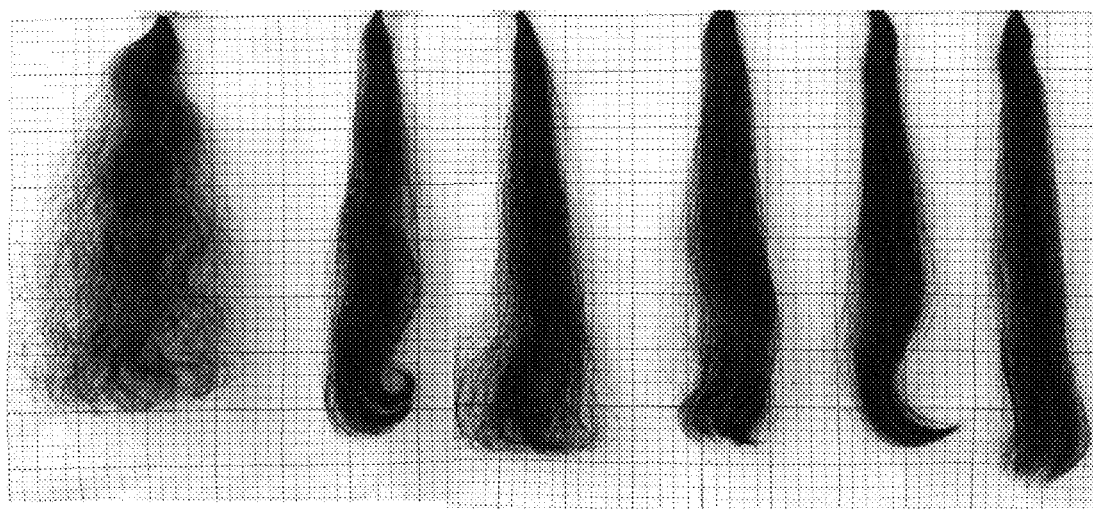
FIG. 4 provides images of hair swatches treated according to one application or treatment cycle including applying inventive or comparative sulfate-free shampoo formulas onto hair and heating the hair at a temperature of equal to or greater than 50° C.
Figure 5:
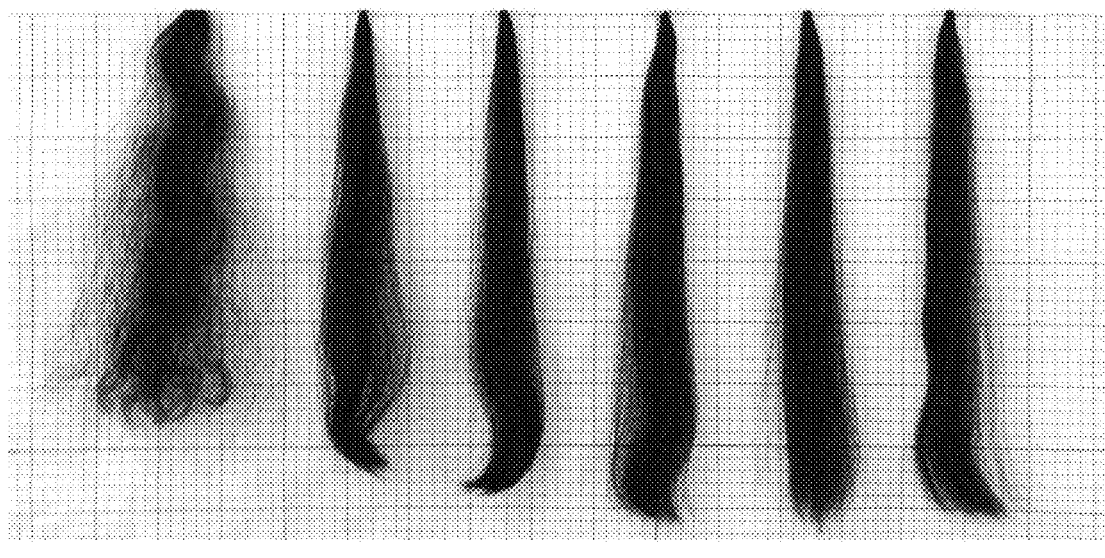
FIG. 5 provides images of hair swatches treated according to two application or treatment cycles including applying inventive or comparative sulfate-free shampoo formulas onto hair and heating the hair at a temperature of equal to or greater than 50° C.
Figure 6:
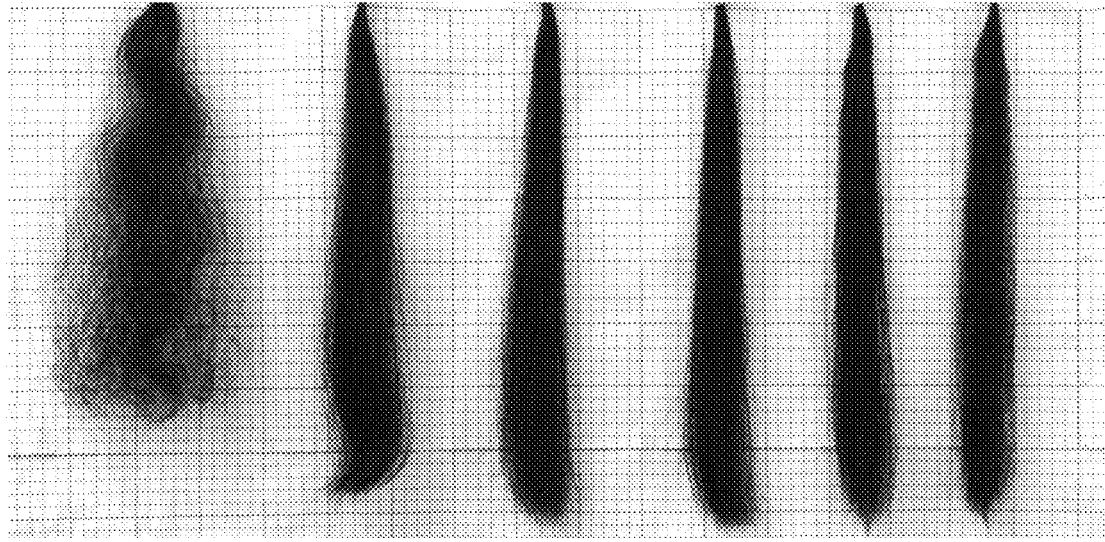
FIG. 6 provides images of hair swatches treated according to five application or treatment cycles including applying inventive or comparative sulfate-free shampoo formulas onto hair and heating the hair at a temperature of equal to or greater than 50° C.

FIGS. 4 to 6 are photographic images of the hair swatches treated with the inventive and comparative sulfate-free shampoo formulas and subjected to several applications or treatment cycles (at $1^{st}$, $2^{nd}$, and $5^{th}$ applications).

I. Sulfate-Based Shampoo Formulas

A. First Application

| Attributes | No treatment (water only) | Comparative Example 1 | Example 2 | Example 3 | Example 4 | Example 5 |
|---|---|---|---|---|---|---|
| Straight | 1.0 | 2.0 | 2.5 | 3.5 | 3.0 | 2.0 |
| Volume | 1.0 | 2.5 | 2.5 | 3.0 | 2.5 | 2.5 |
| Frizz | 1.0 | 2.5 | 3.0 | 3.5 | 3.0 | 2.5 |

Sensorial & Visual Evaluations:
Soft Straightening
Volume Reduction
Frizz Control
Smooth Touch
Cosmeticity
Discipline B. Second Application

| Attributes | No treatment (water only) | Comparative Example 1 | Example 2 | Example 3 | Example 4 | Example 5 |
|---|---|---|---|---|---|---|
| Straight | 1.0 | 2.5 | 3.0 | 3.5 | 3.5 | 2.5 |
| Volume | 1.0 | 2.5 | 2.5 | 3.0 | 3.5 | 2.5 |
| Frizz | 1.0 | 3.0 | 3.0 | 3.5 | 3.5 | 2.5 |

Sensorial & Visual Evaluations
Straightening
Volume Reduction
Frizz Control
Smooth Touch
Cosmeticity
Regularity
Discipline C. Fifth Application

| Attributes | No treatment (water only) | Comparative Example 1 | Example 2 | Example 3 | Example 4 | Example 5 |
|---|---|---|---|---|---|---|
| Straight | 1.0 | 3.5 | 3.0 | 3.5 | 3.5 | 4.0 |
| Volume | 1.0 | 3.0 | 3.5 | 3.5 | 3.5 | 3.5 |
| Frizz | 1.0 | 4.0 | 3.0 | 3.5 | 3.5 | 3.5 |

Sensorial & Visual Evaluations
Straightening
Volume Reduction
Frizz Control
Smooth Touch
Cosmeticity
Regularity
Discipline Summary of Results:

After the $1^{st}$ and $2^{nd}$ applications, the ratings for the hair swatches treated with the inventive formulas at 1, 2.5, and 5% by weight of thiolactic acid were generally higher, if not comparable, to the ratings for the hair treated with the comparative formulas with respect to straightening, volume and frizz. After the $5^{th}$ application, the ratings for the hair swatches treated with the inventive formulas at 2.5, 5, and 8% by weight of thiolactic acid were comparable or higher than the ratings for the hair treated with the comparative formulas with respect to straightening. After the $5^{th}$ application, the ratings for the hair swatches treated with the inventive formulas at 1, 2.5, 5, and 8% by weight of thiolactic acid were higher than the ratings for the hair treated with the comparative formulas with respect to volume. Also, the effects of multiple applications was observed wherein the ratings and the visual appearance of the hair swatches treated with the inventive formulas at 1, 2.5, 5, and 8% by weight of thiolactic acid generally improved, especially at the higher levels of thiolactic acid, from the $1^{st}$ to the $5^{th}$ applications. These results are also evident in FIGS. 1 to 3. While the rest of the results showed lower ratings for the hair treated with the inventive shampoos with respect to some of the attributes at various application cycles and at certain levels of thiolactic acid, the hair treated with the inventive sulfate-based shampoos provided better sensorial (by feel) attributes of cosmeticity and smooth touch as compared to the hair treated with the comparative formula that did not contain thiolactic acid.

II. Sulfate-Free Shampoo Formulas

A. First Application

| Attributes | No treatment (water only) | Comparative Example 6 | Example 7 | Example 8 | Example 9 | Example 10 |
|---|---|---|---|---|---|---|
| Straight | 1.0 | 2.0 | 2.5 | 2.5 | 3.0 | 3.5 |
| Volume | 1.0 | 1.5 | 2.5 | 2.5 | 3.5 | 3.5 |
| Frizz | 1.0 | 2.5 | 3.0 | 2.5 | 3.5 | 3.0 |

Sensorial & Visual Evaluations
Manageability
Volume Reduction
Frizz Control
Smooth Touch
Cosmeticity
Discipline B. Second Application

| Attributes | No treatment (water only) | Comparative Example 6 | Example 7 | Example 8 | Example 9 | Example 10 |
|---|---|---|---|---|---|---|
| Straight | 1.0 | 1.5 | 3.0 | 3.0 | 3.5 | 3.0 |
| Volume | 1.0 | 2.0 | 2.5 | 2.5 | 3.5 | 3.5 |
| Frizz | 1.0 | 3.0 | 3.0 | 3.0 | 3.5 | 3.5 |

Sensorial & Visual Evaluations
Straightening
Volume Reduction
Frizz Control
Smooth Touch
Cosmeticity
Regularity
Discipline C. Fifth Application

| Attributes | No treatment (water only) | Comparative Example 6 | Example 7 | Example 8 | Example 9 | Example 10 |
|---|---|---|---|---|---|---|
| Straight | 1.0 | 2.5 | 3.5 | 3.5 | 4.0 | 4.0 |
| Volume | 1.0 | 3.0 | 3.5 | 4.0 | 3.5 | 3.5 |
| Frizz | 1.0 | 3.0 | 3.5 | 3.5 | 3.0 | 3.0 |

Sensorial & Visual Evaluations
Straightening
Volume Reduction
Frizz Control
Smooth Touch
Cosmeticity
Regularity
Discipline Summary of Results:

After the $1^{st}$ and $2^{nd}$ applications, the ratings for the hair swatches treated with the inventive formulas at 1, 2.5, 5, and 8% by weight of thiolactic acid were higher, if not comparable, to the ratings for the hair treated with the comparative formulas with respect to straightening, volume and frizz. After the $5^{th}$ application, the ratings for the hair swatches treated with the inventive formulas at 1, 2.5, 5, and 8% by weight of thiolactic acid were higher than the ratings for the hair treated with the comparative formula with respect to straightening, volume and frizz. Also, the effects of multiple applications was observed, especially after the $5^{th}$ application wherein the ratings and the visual appearance of the hair swatches treated with the inventive formulas at 1, 2.5, 5, and 8% by weight of thiolactic acid significantly improved from the $1^{st}$ to the $5^{th}$ applications. These effects are also visually evident in FIGS. 4 to 6. While the rest of the results showed lower ratings for the hair treated with the inventive shampoos with respect to some of the attributes at various application cycles and at certain levels of thiolactic acid, the hair treated with the inventive sulfate-based shampoos provided better sensorial (by feel) attributes of cosmeticity, smooth touch, and rough ends as compared to the hair treated with the comparative formula that did not contain thiolactic acid.

Overall, the formulas of the invention imparted hair care and manageability properties to the hair by providing the cosmetic effects of straightening, volume control or reduction, frizz control or less frizziness, cosmetic feel, smooth feel, discipline, regularity and less or reduced rough ends.

The invention claimed is:

1. A hair cosmetic composition for cleansing hair, the hair cosmetic composition comprising:
    a) at least one anionic surfactant in an amount of from 10% to about 20% by weight;
    b) at least one amphoteric surfactant in an amount of from about 0.1% to about 10% by weight;
    c) thiolactic acid, a salt thereof, or a mixture thereof in an amount of from about 0.5% to about 15% by weight;
    d) at least one thickening agent;
    e) at least one nonionic surfactant in an amount of from about 0.01% to about 10% by weight; and
    f) water;
    wherein the pH of the composition ranges from 2 to 4.5, and all weights being relative to the total weight of the cosmetic composition.

2. The hair cosmetic composition according to claim 1, wherein the at least one anionic surfactant is selected from sulfate surfactants, sulfonate surfactants, carboxylic (carboxylate) surfactants, and mixtures thereof.

3. The hair cosmetic composition according to claim 1, wherein the at least one anionic surfactant is selected from sulfate surfactants.

4. The hair cosmetic composition according to claim 1, wherein the at least one anionic surfactant is a sulfate surfactant selected from sodium laureth sulfate, sodium lauryl sulfate, and mixtures thereof.

5. The hair cosmetic composition according to claim 1, wherein the at least one anionic surfactant is selected from sulfonate surfactants, carboxylic (carboxylate) surfactants, and mixtures thereof.

6. The hair cosmetic composition according to claim 1, wherein the at least one anionic surfactant is a sulfonate surfactant selected from sodium lauroyl sarcosinate, sodium lauryl sulfoacetate, sodium isethionate, sodium cocoyl isethionate, disodium laureth sulfosuccinate, sodium lauroyl methyl isethionate, and mixtures thereof.

7. The hair cosmetic composition according to claim 1, wherein the at least one amphoteric surfactant is selected from (C8-C20)alkylbetaines, (C8-C20)alkylamido (C1-C6) alkylbetaines, sulfobetaines, (C8-C20)alkylsulfobetaines, (C8-C20)alkylamido(C1-C6)alkylsulfobetaines, (C8-C20) alkylamphoacetate, (C8-C20)alkylamphodiacetate, and their salts, and mixtures thereof.

8. The hair cosmetic composition according to claim 1, wherein the at least one amphoteric surfactant (b) is selected from coco-betaine, cocamidopropylbetaine, sodium cocoamphoacetate, disodium cocoamphodiacetate, and mixtures thereof.

9. The hair cosmetic composition according to claim 1, wherein the at least one thiol-based compound is selected from thiolactic acid.

10. The hair cosmetic composition according to claim 1, wherein the at least one thickening agent is selected from cellulose polymers, gums, modified or unmodified carboxyvinyl polymers, polyacrylamides, copolymers of acrylic acid and of acrylamide, sodium salts of polyhydroxycarboxylic acids, optionally crosslinked and/or neutralized 2-acrylamido-2-methylpropanesulphonic acid polymers and copolymers, polyacrylic acid/alkyl acrylate, glucans, modified or unmodified starches, silicas, potato starch modified, and mixtures thereof in an amount of from about 0.01% to about 5% by weight, relative to the total weight of the composition.

11. The hair cosmetic composition according to claim 1, wherein the at least one nonionic surfactant is selected from fatty alcohols, alkoxylated fatty alcohols, alkyl(ether)phosphates, alkylpolyglucosides, fatty acid alkanolamides, and mixtures thereof in an amount of from about 0.01% to about 10% by weight, relative to the total weight of the composition.

12. The hair cosmetic composition according to claim 1, further comprising at least one cationic conditioning polymer selected from cationic cellulose derivatives, cationic gum derivatives, polymer derivatives of diallyldimethyl ammonium chloride, polymer derivatives of methacrylamidopropyltrimethylammonium chloride, and mixtures thereof in an amount of from about 0.01% to about 4% by weight, relative to the total weight of the composition.

13. The composition, according to claim 1, further comprising at least one neutralizing agent selected from organic amines, alkali metal hydroxides, alkali earth metal hydroxides, alkali metal carbonates, alkali metal phosphates, and mixtures thereof.

14. A method of treating hair, the method comprising a treatment cycle involving the steps of:
a) optionally, washing/rinsing the hair with a shampoo having a neutral pH and/or rinsing the hair with water, followed by allowing the hair to air dry, while optionally applying a smoothing action on the hair;
b) applying the composition of claim 1 onto the hair;
c) allowing the composition in b) to remain on the hair for a period of time ranging from about 1 to about 10 minutes or from about 1 to about 5 minutes;
d) rinsing the hair with water;
e) drying the hair at a temperature ranging from room temperature up to about 100° C., while optionally applying a smoothing action on the hair;
f) passing a flat iron over the hair swatch at least once; and
g) washing/rinsing the hair with a shampoo having a neutral pH and/or rinsing the hair with water, followed by allowing the hair to air dry, while optionally applying a smoothing action on the hair.

15. The method according to claim 14, wherein the treatment cycle is repeated over a period of days.

16. The hair cosmetic composition according to claim 1 being free of chitosan.

17. The hair cosmetic composition according to claim 1, wherein the at least one thickening agent is chosen from hydroxyethylcellulose, cetyl hydroxyethylcellulose, carbomers, and mixtures thereof.

18. A hair cosmetic composition comprising:
a) at least one anionic surfactant selected from sulfate surfactants in an amount of from 10% to about 18% by weight;
b) at least one amphoteric surfactant selected from (C8-C20)alkylbetaines in an amount of from about 0.8% to about 6% by weight;
c) thiolactic acid, a salt thereof, or a mixture thereof in an amount of from about 0.7% to about 12% by weight;
d) at least one thickening agent selected from hydroxyethylcellulose (also known as HEC), hydroxymethylcellulose, methylhydroxyethylcellulose, hydroxypropylcellulose (also known as HPC), hydroxybutylcellulose, hydroxyethylmethylcellulose (also known as methyl hydroxyethylcellulose) and hydroxypropylmethylcellulose (also known as HPMC), cetyl hydroxyethylcellulose, hydroxypropyl guar gums, acrylate/C10 C30 alkyl acrylate copolymers, carbomers, polyacrylates, potato starch modified, and mixtures thereof in an amount of from about 0.05% to about 1% by weight;
e) at least one nonionic surfactant selected from fatty alcohols, alkoxylated fatty alcohols, alkyl(ether)phosphates, alkylpolyglucosides, fatty acid alkanolamides, and mixtures thereof;
f) water;
g) optionally, at least one cationic conditioning polymer; and
h) optionally, at least one neutralizing agent;
wherein the pH of the composition ranges from about pH 3 to 4.5; and
all weights being relative to the total weight of the cosmetic composition.

19. A hair cosmetic composition comprising:
a) at least one anionic surfactant selected from sulfonate surfactants, carboxylic (carboxylate) surfactants, and mixtures thereof in an amount of from 10% to about 18% by weight;
b) at least one amphoteric surfactant selected from (C8-C20)alkylbetaines, (C8-C20)alkylamido (C1-C6)alkylbetaines, sulfobetaines, (C8-C20)alkylsulfobetaines, (C8-C20)alkylamido(C1-C6)alkylsulfobetaines, (C8-C20)alkylamphoacetate, (C8-C20)alkylamphodiacetate, and their salts, and mixtures thereof in an amount of from about 0.8% to about 6% by weight;
c) thiolactic acid, a salt thereof, or a mixture thereof in an amount of from about 0.7% to about 12% by weight;
d) at least one thickening agent selected from hydroxyethylcellulose (also known as HEC), hydroxymethylcellulose, methylhydroxyethylcellulose, hydroxypropylcellulose (also known as HPC), hydroxybutylcellulose, hydroxyethylmethylcellulose (also known as methyl hydroxyethylcellulose) and hydroxypropylmethylcellulose (also known as HPMC), cetyl hydroxyethylcellulose, hydroxypropyl guar gums, acrylate/C10 C30 alkyl acrylate copolymers, carbomers, polyacrylates, potato starch modified, and mixtures thereof in an amount of from about 0.05% to about 1% by weight;
e) at least one nonionic surfactant selected from fatty alcohols, alkoxylated fatty alcohols, alkyl(ether)phosphates, alkylpolyglucosides, fatty acid alkanolamides, and mixtures thereof;
f) water;
g) optionally, at least one cationic conditioning polymer; and
h) optionally, at least one neutralizing agent;

wherein the pH of the composition ranges from about pH 3 to 4; and all weights being relative to the total weight of the cosmetic composition.

* * * * *